United States Patent
Horiuchi

(10) Patent No.: US 6,987,828 B2
(45) Date of Patent: Jan. 17, 2006

(54) TRANSMITTED X-RAY DATA ACQUISITION SYSTEM AND X-RAY COMPUTED TOMOGRAPHY SYSTEM

(75) Inventor: Tetsuya Horiuchi, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 260 days.

(21) Appl. No.: 10/397,026

(22) Filed: Mar. 25, 2003

(65) Prior Publication Data

US 2003/0185343 A1 Oct. 2, 2003

(30) Foreign Application Priority Data

Mar. 27, 2002 (JP) .............................. 2002-088003

(51) Int. Cl.
*A61B 6/00* (2006.01)

(52) U.S. Cl. ........................................ 378/16; 378/108
(58) Field of Classification Search ................ 378/108, 378/16, 25, 8, 95
See application file for complete search history.

(56) References Cited

U.S. PATENT DOCUMENTS

| | | | | |
|---|---|---|---|---|
| 5,379,333 | A | * | 1/1995 | Toth ............................. 378/16 |
| 5,400,378 | A | * | 3/1995 | Toth ............................. 378/16 |
| 5,485,494 | A | | 1/1996 | Williams et al. |
| 5,867,555 | A | | 2/1999 | Popescu et al. |
| 6,018,563 | A | | 1/2000 | Arai et al. |
| 6,067,341 | A | * | 5/2000 | Horiuchi ........................ 378/8 |
| 6,285,741 | B1 | | 9/2001 | Ackelsberg et al. |
| 6,404,844 | B1 | | 6/2002 | Horiuchi et al. |

FOREIGN PATENT DOCUMENTS

JP 11237280 8/1999

OTHER PUBLICATIONS

International Search Report, dated Oct. 16, 2003, Application No. EP 03 25 1939, 3 pages.

* cited by examiner

Primary Examiner—Edward J. Glick
Assistant Examiner—Elizabeth Keaney
(74) Attorney, Agent, or Firm—Carl B. Horton, Esq.; Armstrong Teasdale LLP

(57) ABSTRACT

An object of the present invention is to acquire transmitted X-ray data by irradiating X-rays of appropriate doses determined for the portions of a section containing the major axis and the portions thereof containing the minor axis respectively. An X-ray irradiating/detecting device consists mainly of an X-ray irradiator that includes an X-ray tube and irradiates a fan-shaped X-ray beam, and an X-ray detector that has a plurality of X-ray detecting elements arrayed in a direction in which the fan-shaped X-ray beam spreads and that is opposed to the X-ray irradiator with an object of imaging between them. The X-ray irradiating/detecting device is rotated about the object in order to acquire transmission X-ray data stemming from a plurality of views. At this time, the dose of the X-ray beam is differentiated between predetermined angular ranges of a section of the object shaped like an oval, which extend with the minor axis of the oval section as a centerline, and the other angular ranges.

14 Claims, 17 Drawing Sheets

24
X-ray detecting element
24(i)

TRANSMITTED X-RAY DATA ACQUISITION SYSTEM AND X-RAY COMPUTED TOMOGRAPHY SYSTEM

This application claims the benefit of Japanese Application No. 2002-088003 filed Mar. 27, 2002.

BACKGROUND OF THE INVENTION

The present invention relates to a transmitted X-ray data acquisition system and an X-ray computed tomography system. More specifically, the present invention relates to a system for acquiring transmitted X-ray data based on which an X-ray tomographic image is produced, and an X-ray computed tomography system for producing the tomographic image on the basis of the acquired transmitted X-ray data.

In X-ray computed tomography systems, an X-ray irradiating/detecting device acquires transmitted X-ray data that represents X-rays transmitted by an object of imaging, and a tomographic image of the object is produced (reconstructed) based on the transmitted X-ray data. The X-ray irradiator irradiates an X-ray beam that spreads (has a width large enough) to cover a tomographic layer of the object or a radiographic section thereof and has a thickness in a direction perpendicular to the direction of the layer or section. The X-ray detector is a multi-channel X-ray detector that has a plurality of X-ray detecting elements arrayed and detects the X-ray beam. The X-ray irradiating/detecting device is rotated about the object (in order to scan the object) in order to acquire projection data, that is, transmitted X-ray data in a plurality of directions determined for respective views around the object. A tomographic image is then reconstructed based on the acquired transmitted X-ray data items by means of a computer.

In order to produce a high-quality tomographic image, the conditions for X-irradiation are adjusted depending on an object. When an object exhibits a larger absorption dose, the object is imaged with X-rays of a larger radiation dose. The radiation dose of X-rays is determined with a product of a tube current by a conduction time, that is, a milliampere-per-second (mAs) value.

An image standard deviation (image SD) is adopted as one of indices indicating the quality of a reconstructed image. The image SD exhibits a strong correlation with a projection area in an object whose projection is created as long as the product of a tube current flowing through an X-ray tube by a conduction time remains constant. In order to produce a tomographic image exhibiting a proper image SD, the product of a tube current by a conduction time is automatically adjusted depending on the projection area. For the automatic adjustment of the product of a tube current by a conduction time, X-ray fluoroscopy is performed in advance in order to determine a projection area, and the product of a tube current by a conduction time is appropriately determined depending on the size of the projection area.

Sections of a human body that is an object of imaging are generally oval. An X-ray absorption dose differs between the major-axis directions of the section and the minor-axis directions thereof, the product of a tube current by a conduction time determined as mentioned above is corrected based on an oval ratio, that is, a ratio of the major axis to the minor axis. Due to the correction, the larger the oval ratio, the larger the product of a tube current by a conduction time.

In order to measure the lengths of the major and minor axes, X-ray fluoroscopy is performed by irradiating X-rays to the object in the anteroposterior or posteroanterior direction (at 0° or 180° to an X-ray tube) and in a transverse direction (at 90° or 270° thereto). The 0° or 180° direction corresponds to the anteroposterior or posteroanterior direction, and the 90° or 270° direction corresponds to the transverse direction. The lengths of lines passing the center of a projection created with X-rays irradiated in each of the anteroposterior or posteroanterior direction and the transverse direction are measured. The longer one of the lines is regarded as the major axis and the shorter one is regarded as the minor axis. Consequently, the oval ratio is calculated.

The X-ray irradiating/detecting device is rotated along a helical trajectory, whereby helical scanning is achieved. During the helical scanning, an object is scanned continuously over a predetermined length in a body-axis direction thereof. Therefore, a plurality of tomographic images representing sections of the object that extend at different slicing positions on the body axis can be reconstructed based on acquired transmitted X-ray data.

During helical scanning, the positions on a body axis which X-rays pass vary continuously during rotation of the X-ray irradiating/detecting device. Therefore, the product of a tube current by a conduction time is adjusted depending on a projection area in an object that extends at an intermediate scanning position. What is referred to as the intermediate scanning position is a position on the body axis which X-rays pass at an intermediate time point within one rotation.

A radiation dose dependent on the product of a tube current by a conduction time that is corrected based on an oval ratio is retained at the same value during one rotation of the X-ray irradiating/detecting device about an object. The dose is appropriate for the portions of a section containing the major axis thereof but is excessive to the portions thereof containing the minor axis thereof. Consequently, a total dose is too large and excessive X-rays are irradiated.

Assume that helical scanning is performed by moving the X-ray irradiating/detecting device by a long distance along a body axis during one rotation, that is, helical scanning is performed by moving the X-ray irradiating/detecting device in units of a large pitch. In this case, a variation of a projection area in an object whose projection is created during one rotation tends to increase. The product of a tube current by a conduction time determined relative to the intermediate scanning position is not always appropriate for the other positions.

SUMMARY OF THE INVENTION

Therefore, an object of the present invention is to provide a system for acquiring transmitted X-ray data by irradiating X-rays of appropriate doses associated with the portions of a section containing the major axis thereof and the portions thereof containing the minor axis thereof, and an X-ray computed tomography system for producing a tomographic image on the basis of the thus acquired transmitted X-ray data.

Another object of the present invention is to provide a system for acquiring transmitted X-ray data by irradiating X-rays of an appropriate dose even when helical scanning is performed by moving an X-ray tube in units of a large pitch, and an X-ray computed tomography system for producing a tomographic image on the basis of the thus acquired transmitted X-ray data.

(1) According to one aspect of the present invention that attempts to solve the above problems, there is provided a transmitted X-ray data acquisition system consisting mainly of: a data acquiring means for rotating an X-ray irradiating/detecting device, which includes an X-ray irradiator that has an X-ray tube and irradiates a fan-shaped X-ray beam and an X-ray detector that has a plurality of X-ray detecting elements arrayed in a direction in which the fan-shaped X-ray beam spreads and that is opposed to the X-ray irradiator with an object of imaging between them, about the object so as to acquire transmitted X-ray data stemming from a plurality of views; and a dose adjusting means that differentiates the dose of the X-ray beam between predetermined angular ranges of a section of the object shaped like an oval, which extend with the minor axis as a centerline, and the other angular ranges thereof.

(2) According to another aspect of the present invention that attempts to solve the above problems, there is provided a transmitted X-ray data acquisition method characterized in that: when an X-ray irradiating/detecting device including an X-ray irradiator that has an X-ray tube and irradiates a fan-shaped X-ray beam and an X-ray detector that has a plurality of X-ray detecting elements arrayed in a direction in which the fan-shaped X-ray beam spreads and that is opposed to the X-ray irradiator with an object of imaging between them is rotated about the object in order to acquire transmitted X-ray data stemming from a plurality of views, the dose of the X-ray beam is differentiated between predetermined angular ranges of a section of the object shaped like an oval, which extend with the minor axis of the section as a centerline, and the other angular ranges thereof.

(3) According to another aspect of the present invention that attempts to the aforesaid problems, there is provided an X-ray computed tomography system consisting mainly of: a data acquiring means that rotates an X-ray irradiating/detecting device, which includes an X-ray irradiator that has an X-ray tube and irradiates a fan-shaped X-ray beam and an X-ray detector that has a plurality of X-ray detecting elements arrayed in a direction in which the fan-shaped X-ray beam spreads and that is opposed to the X-ray irradiator with an object of imaging between them, about the object so as to acquire transmitted X-ray data stemming from a plurality of views; a dose adjusting means that differentiates the does of the X-ray beam between predetermined angular ranges of a section of the object shaped like an oval, which extend with the minor axis of the section as a centerline, and the other angle-of-rotation ranges thereof; and an image producing means for producing an image on the basis of the transmitted X-ray data.

(4) According to still another aspect of the present invention that attempts to solve the aforesaid problems, there is provided an X-ray computed tomography method characterized in that: when an X-ray irradiating/detecting device including an X-ray irradiator that has an X-ray tube and irradiates a fan-shaped X-ray beam and an X-ray detector that has a plurality of X-ray detecting elements arrayed in a direction in which the fan-shaped X-ray beam spreads and that is opposed to the X-ray irradiator with an object of imaging between them is rotated about the object in order to acquire transmitted X-ray data stemming from a plurality of views, an image is produced based on the transmitted X-ray data; and the dose of the X-ray beam is differentiated between predetermined angular ranges of a section of the object shaped like an oval, which extend with the minor axis of the section as a centerline, and the other angle-of-rotation ranges thereof.

According to the aspects of the present invention described in clauses (1) to (4), the X-ray irradiating/detecting device including an X-ray irradiator that has an X-ray tube and irradiates a fan-shaped X-ray beam, and an X-ray detector that has a plurality of X-ray detecting elements arrayed in a direction in which the fan-shaped X-ray beam spreads and that is opposed to the X-ray irradiator with an object of imaging between them is rotated about the object in order to acquire transmitted X-ray data stemming from a plurality of views. At this time, the dose of the X-ray beam is differentiated between predetermined angle-of-rotation ranges of a section of the object shaped like an oval, which extend with the minor axis of the section as a centerline, and the other angle-of-rotation ranges thereof. Consequently, transmitted X-ray data can be acquired by irradiating X-rays of appropriate doses determined for the portions of the section containing the major axis thereof and the portions thereof containing the minor axis thereof respectively.

Preferably, when the section of the object is shaped like an oval, the predetermined angular ranges are adjusted based on the compression of the oval section. In this case, transmitted X-ray data can be acquired by irradiating X-rays of appropriate doses determined for the portions of the section containing the major axis thereof and the portions thereof containing the minor axis thereof respectively.

Preferably, the required dose of the X-ray beam is calculated in advance for each position on the object's body axis, which the X-ray beam passes, on the assumption that the section of the object is shaped like an oval or on the assumption that the section thereof is shaped like a circle. Either of the calculated dose values is selected depending on the angular ranges to either of which the X-ray irradiating/detecting device is moved by an angle of rotation. In this case, the dose can be adjusted appropriately irrespective of the initial value the angle of rotation of the X-ray irradiating/detecting device assumes at the start of helical scanning.

Preferably, the required dose is calculated based on an image SD predicted from a projection of the object created with X-rays. Thus, an appropriate dose can be calculated.

Preferably, the target image SD can be manually adjusted so that the quality of an image produced based on transmitted X-ray data can be controlled.

Preferably, the dose is adjusted based on a tube current flowing through the X-ray tube. In this case, the dose adjustment is easy to do.

Preferably, the X-ray irradiating/detecting device is rotated about the object along a helical trajectory. In this case, during helical scanning, transmitted X-ray data can be acquired by irradiating X-rays of appropriate doses determined for the portions of a section of the object containing the major axis thereof and the portions thereof containing the minor axis thereof respectively.

(5) According to another aspect of the present invention that attempts to solve the aforesaid problems, there is provided a transmitted X-ray data acquisition system consisting mainly of: a data acquiring means that rotates an X-ray irradiating/detecting device, which includes an X-ray irradiator that has an X-ray tube and irradiates a fan-shaped X-ray beam and an X-ray detector that has a plurality of X-ray detecting elements arrayed in a direction in which the fan-shaped X-ray beam spreads and that is opposed to the X-ray irradiator with an object of imaging between them, about the object along a helical trajectory so as to acquire transmitted X-ray data stemming from a plurality of view; and a dose adjusting means that adjusts the dose of the X-ray beam for each rotational extent smaller than one rotation to be made by the X-ray irradiating/detecting device.

(6) According to another aspect of the present invention that attempts to solve the aforesaid problems, there is provided a transmitted X-ray data acquisition method characterized in that: when an X-ray irradiating/detecting device including an X-ray irradiator that has an X-ray tube and irradiates a fan-shaped X-ray beam and an X-ray detector that has a plurality of X-ray detecting elements arrayed in a direction in which the fan-shaped X-ray beam spreads and that is opposed to the X-ray irradiator with an object of imaging between them is rotated about the object along a helical trajectory in order to acquire transmitted X-ray data stemming from a plurality of views, the dose of the X-ray beam is adjusted for each rotational extent smaller than one rotation.

(7) According to another aspect of the present invention that attempts to solve the aforesaid problems, there is provided an X-ray computed tomography system consisting mainly of: a data acquiring means that rotates an X-ray irradiating/detecting device, which includes an X-ray irradiator that has an X-ray tube and irradiates a fan-shaped X-ray beam and an X-ray detector that has a plurality of X-ray detecting devices arrayed in a direction in which the fan-shaped X-ray beam spreads and that is opposed to the X-ray irradiator with an object of imaging between them, about the object along a helical trajectory so as to acquire transmitted X-ray data stemming from a plurality of views; a dose adjusting means that adjusts the dose of the X-ray beam for each rotational extent smaller than one rotation of the X-ray irradiating/detecting device; and an image producing means that produces an image on the basis of the transmitted X-ray data.

(8) According to another aspect of the present invention that attempts to solve the aforesaid problems, there is provided an X-ray computed tomography method characterized in that: when an X-ray irradiating/detecting device including an X-ray irradiator that has an X-ray tube and irradiates a fan-shaped X-ray beam and an X-ray detector that has a plurality of X-ray detecting elements arrayed in a direction in which the fan-shaped X-ray beam spreads and that is opposed to the X-ray irradiator with an object of imaging between them is rotated about the object along a helical trajectory in order to acquire transmitted X-ray data stemming from a plurality of views, an image is produced based on the transmitted X-ray data; and the dose of the X-ray beam is adjusted for each rotational extent smaller than one rotation.

According to the aspects of the present invention described in clauses (5) to (8), an X-ray irradiating/detecting device including an X-ray irradiator that has an X-ray tube and irradiates a fan-shaped X-ray beam and an X-ray detector that has a plurality of X-ray detecting elements arrayed in a direction in which the fan-shaped X-ray beam spreads and that is opposed to the X-ray irradiator with an object of imaging between them is rotated about the object along a helical trajectory in order to acquire transmitted X-ray data stemming from a plurality of views. At this time, the dose of the X-ray beam is adjusted for each rotational extent smaller than one rotation. Even when helical scanning is performed with the helical scan pitch set to a large value, transmitted X-ray data can be acquired by irradiating X-rays of an appropriate dose.

Preferably, a detector having a plurality of rows of detecting elements, each of which has a plurality of X-ray detecting elements arrayed in a direction in which the fan-shaped X-ray beam spreads, arranged in the direction of the thickness of the fan-shaped X-ray beam is adopted as the X-ray detector. In this case, helical scanning to be performed with the helical scan pitch set to a large value can be efficiently achieved According to the present invention, there are provided a system capable of acquiring transmitted X-ray data by irradiating X-rays of appropriate doses determined for the portions of a section containing the major axis and the portions thereof containing the minor axis respectively, and an X-ray computed tomography system capable of producing a tomographic image on the basis of the thus acquired transmitted X-ray data.

Moreover, there are provided a system capable of acquiring transmitted X-ray data by irradiating X-rays of an appropriate dose even when helical scanning is performed with the helical scan pitch set to a large value, and an X-ray computed tomography system capable of producing a tomographic image on the basis of the thus acquired transmitted X-ray data.

Further objects and advantages of the present invention will be apparent from the following description of the preferred embodiments of the invention as illustrated in the accompanying drawings.

DETAILED DESCRIPTION OF THE INVENTION

Figure 1:
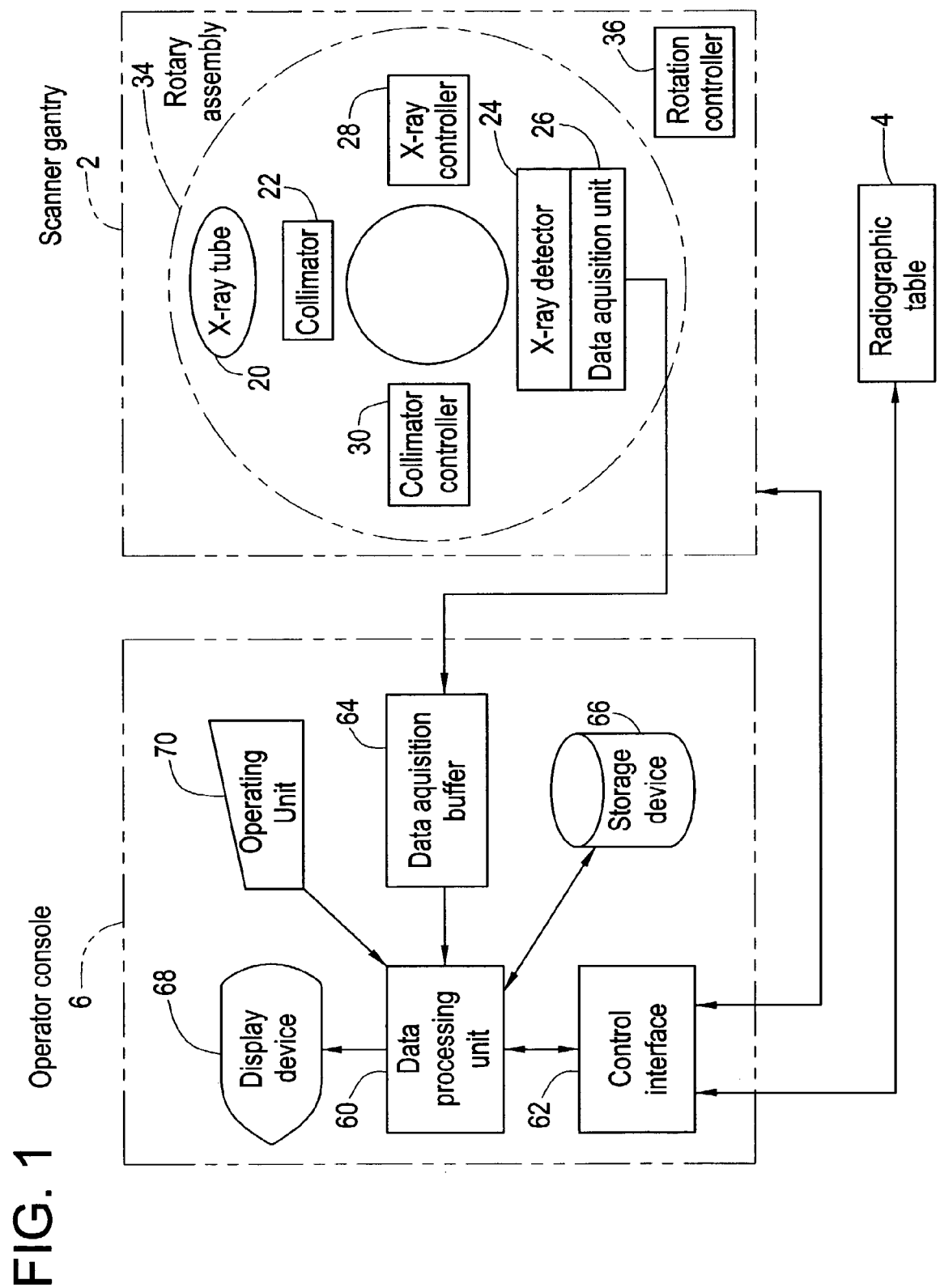
FIG. 1 is a block diagram showing a system of an example of an embodiment of the present invention.

An embodiment of the present invention will be described with reference to the drawings below. FIG. 1 is a block diagram showing an X-ray computed tomography (X-ray CT) system. The present system is an example of an embodiment of the present invention. The configuration of the present system provides an example of an embodiment of an X-ray computed tomography system in which the present invention is implemented. The actions of the present system provide an example of an embodiment of an X-ray computed tomography method in which the present invention is implemented.

As shown in FIG. 1, the present system consists mainly of a scanner gantry 2, a radiographic table 4, and an operator console 6. The scanner gantry 2 includes an X-ray tube 20. X-rays radiated from the X-ray tube 20 and not shown are recomposed into a fan-shaped X-ray beam, that is, a fan beam by means of a collimator 22, and irradiated to an X-ray detector 24. The X-ray tube 20 and collimator 22 constitute an example of an embodiment of an X-ray irradiator included in the present invention.

The X-ray detector 24 has a plurality of detecting elements arrayed in a direction in which the fan-shaped X-ray beam spreads. The X-ray detector 24 is an example of an embodiment of an X-ray detector included in the present invention. The configuration of the X-ray detector 24 will be described later.

The X-ray tube 20, collimator 22, and X-ray detector 24 constitutes an X-ray irradiating/detecting device. The X-ray irradiating/detecting device is an example of an embodiment of an X-ray irradiating/detecting device included in the present invention. The X-ray irradiating/detecting device will be described later.

A data acquisition unit 26 is connected to the X-ray detector 24. The data acquisition unit 26 acquires detection signals produced by the detecting elements included in the X-ray detector 24 in the form of digital data.

An X-ray controller 28 controls radiation of X-rays from the X-ray tube 20. The illustration of the connection between the X-ray tube 20 and X-ray controller 28 will be omitted. A collimator controller 30 controls the collimator 22. The illustration of the connection between the collimator 22 and collimator controller 30 will be omitted.

The foregoing components started with the X-ray tube and ended with the collimator controller 30 are encased in a rotary assembly 34 of the scanner gantry 2. A rotation controller 36 controls the rotation of the rotary assembly 34. The illustration of the connection between the rotary assembly 34 and rotation controller 36 will be omitted.

The radiographic table 4 is used to carry an object of imaging, which is not shown, into or out of an X-ray irradiation space of the scanner gantry 2. The relationship between the object and X-ray irradiation space will be described later.

The operator console 6 includes a data processing unit 60. The data processing unit 60 is realized with, for example, a computer. A control interface 62 is connected to the data processing unit 60. The scanner gantry 2 and radiographic table 4 are connected to the control interface 62. The data processing unit 60 controls the scanner gantry 2 and radiographic table 4 via the control interface 62.

The data acquisition unit 26, X-ray controller 28, collimator controller 30, and rotation controller 36 included in the scanner gantry 2 are controlled via the control interface 62. The illustration of the connections of the components to the control interface 62 will be omitted.

A data acquisition buffer 64 is connected to the data processing unit 60. The data acquisition unit 26 included in the scanner gantry 2 is connected to the data acquisition buffer 64. Data acquired by the data acquisition unit 26 is transferred to the data processing unit 60 via the data acquisition buffer 64.

The data processing unit 60 reconstructs an image using transmitted X-ray data that is acquired via the data acquisition buffer 64 and that stems from a plurality of views. For image reconstruction, for example, a filtered back-projection method is adopted. The data processing unit 60 is an example of an embodiment of an image producing means included in the present invention.

A storage device 66 is connected to the data processing unit 60. Various kinds of data items and programs are stored in the storage device 66. The data processing unit 60 runs the programs stored in the storage device 66, whereby various kinds of data processing concerning radiography are carried out.

A display device 68 and an operating unit 70 are connected to the data processing unit 60. A reconstructed image and other information produced by the data processing unit 60 are displayed on the display device 68. A user handles the operating unit 70 so as to enter various instructions or information that will be transferred to the data processing unit 60. The user uses the display device 68 and operating unit 70 to operate the X-ray CT system interactively.

Figure 2:
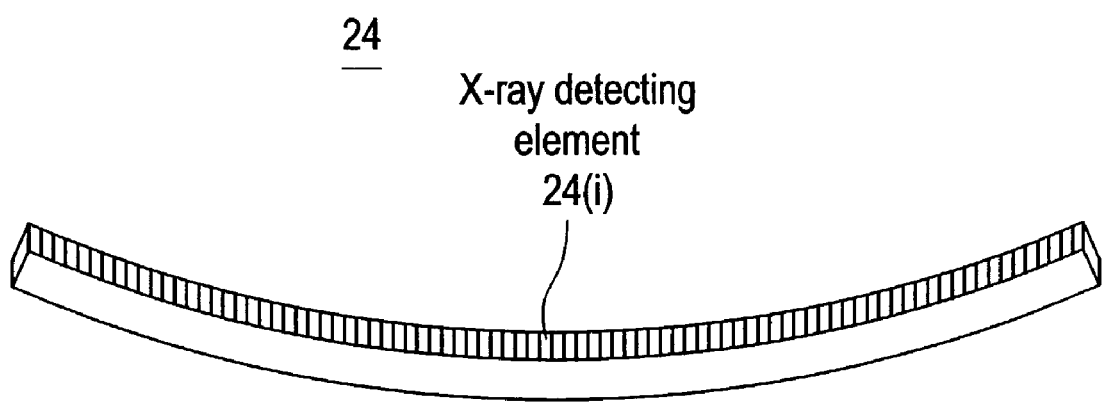
FIG. 2 picturesquely shows an X-ray detector.

FIG. 2 picturesquely shows the structure of the X-ray detector 24. As illustrated, the X-ray detector 24 is a multi-channel X-ray detector having numerous X-ray detecting elements 24($i$) arrayed one-dimensionally. Herein, i denotes a channel number and ranges, for example, from 1 to 1000. The X-ray detecting elements 24($i$) form an X-ray incidence surface that is curved like the concave surface of a cylinder.

Figure 3:
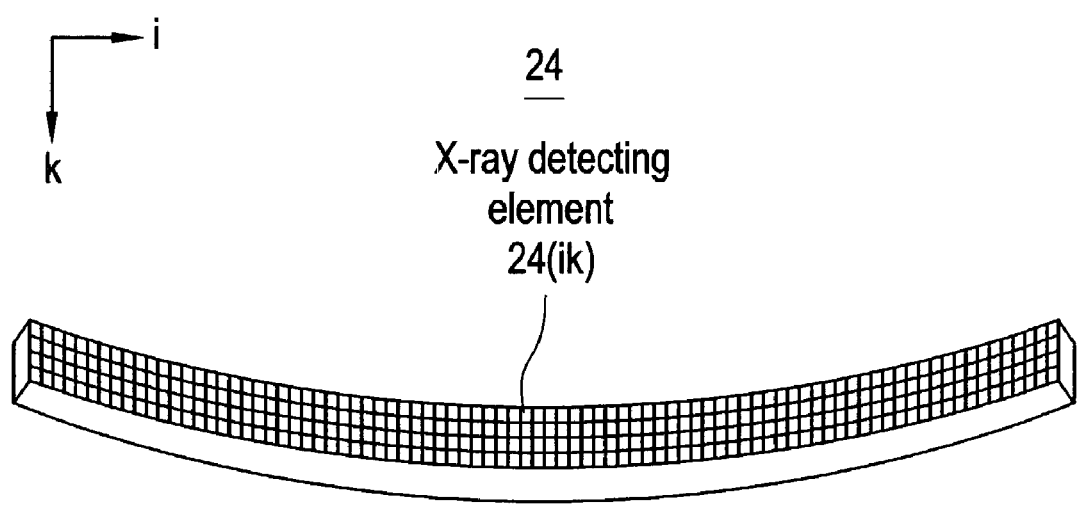
FIG. 3 picturesquely shows an X-ray detector.

The X-ray detector 24 may have, as shown in FIG. 3, a plurality of X-ray detecting elements 24($ik$) arrayed two-dimensionally. The X-ray detecting elements 24($ik$) form an X-ray incidence surface that is curved like the concave surface of a cylinder. Herein, k denotes a row number of, for example, 1, 2, 3, or 4. The row of X-ray detecting elements 24($ik$) having the row number k is composed of identical detecting elements. The number of rows of detecting elements constituting the X-ray detector 24 is not limited to 4. Alternatively, the number of rows of detecting elements may be larger or smaller.

The X-ray detecting elements 24($ik$) are each made of a combination of, for example, a scintillator and a photodiode. Alternatively, a semiconductor X-ray detecting element made of, for example, cadmium telluride (CdTe) or an ionization chamber-type X-ray detecting element utilizing a xenon gas may be adopted as the X-ray detecting elements 24($ik$).

Figure 4A:
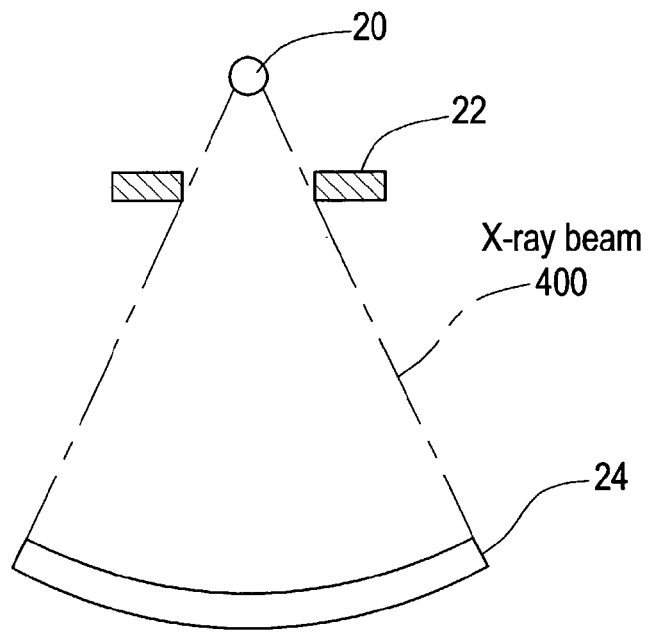
FIG. 4 picturesquely shows an X-ray irradiating/detecting device.
Figure 4B:
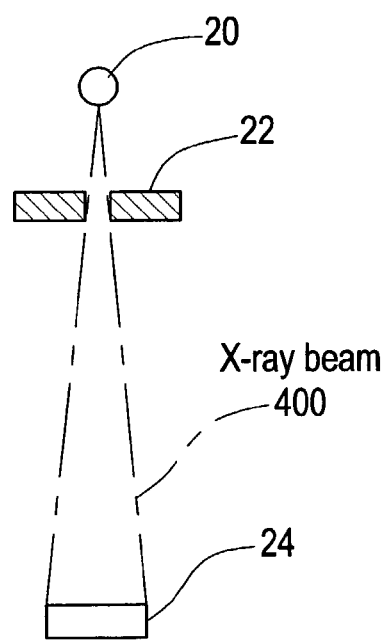

FIG. 4a and FIG. 4b show the correlation among the X-ray tube 20, collimator 22, and X-ray detector 24 which constitute the X-ray irradiating/detecting device. FIG. 4a is a front view of the scanner gantry 2, and FIG. 4b is a side view thereof. As illustrated, X-rays radiated from the X-ray tube 20 are recomposed into a fan-shaped X-ray beam 400 by means of the collimator 22 and irradiated to the X-ray detector 24.

FIG. 4a shows the spread of the fan-shaped X-ray beam 400. The direction in which the X-ray beam 400 spreads corresponds to the direction in which the channels of the X-ray detector 24 are arrayed. FIG. 4b shows the thickness of the X-ray beam 400. The direction of the thickness of the X-ray beam 400 corresponds to the direction in which the plurality of rows of detecting elements constituting the X-ray detector 24 is juxtaposed.

Figure 5:
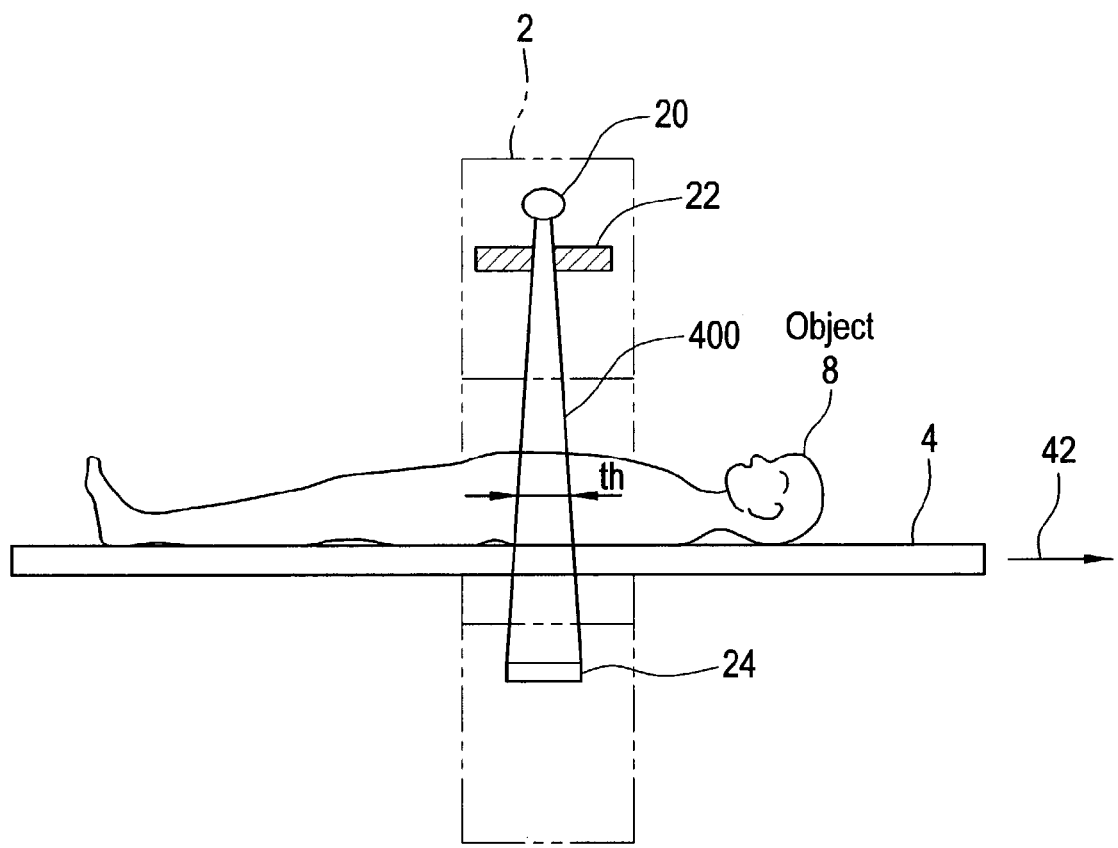
FIG. 5 picturesquely shows the X-ray irradiating/detecting device.

An object 8 lying down on the radiographic table 4 is, for example, as shown in FIG. 5, carried into the X-ray irradiation space while the body axis thereof is intersecting the fan plane of the X-ray beam 400. The scanner gantry 2 has a cylindrical hollow structure to accommodate the X-ray irradiating/detecting device internally.

The X-ray irradiation space is realized with the bore of the cylindrical structure of the scanner gantry 2. An image of the object 8 sliced with the X-ray beam 400 is projected on the X-ray detector 24. The X-ray detector 24 detects X-rays transmitted by the object 8. The thickness th of the X-ray beam 400 to be irradiated to the object 8 is adjusted by changing the aperture of the collimator 22.

The X-ray irradiating/detecting device composed of the X-ray tube 20, collimator 22, and X-ray detector 24 continuously rotates about (scans) the body axis of the object 8 with the correlation among the X-ray tube, collimator, and X-ray detect or maintained. When the radiographic table 4 is continuously moved along the body axis of the object 8 concurrently with the rotation of the X-ray irradiating/detecting device, the X-ray irradiating/detecting device rotates about the object 8 while drawing a helical trajectory relatively to the object 8. Thus, so-called helical scanning is carried out. When the object is scanned with the radiographic table 4 at a standstill, axial transverse scanning is carried out, that is, scanning is performed with slicing positions fixed.

Projection data stemming from a plurality of views (for example, about 1000 views) is acquired during one scan or one rotation. Acquisition of projection data is achieved by a combination of the X-ray detector 24, data acquisition unit 26, and data acquisition buffer 64. The scanner gantry 2 and radiographic table 4 that are involved in data acquisition constitute an example of a transmitted X-ray data acquiring means included in the present invention.

Figure 6:
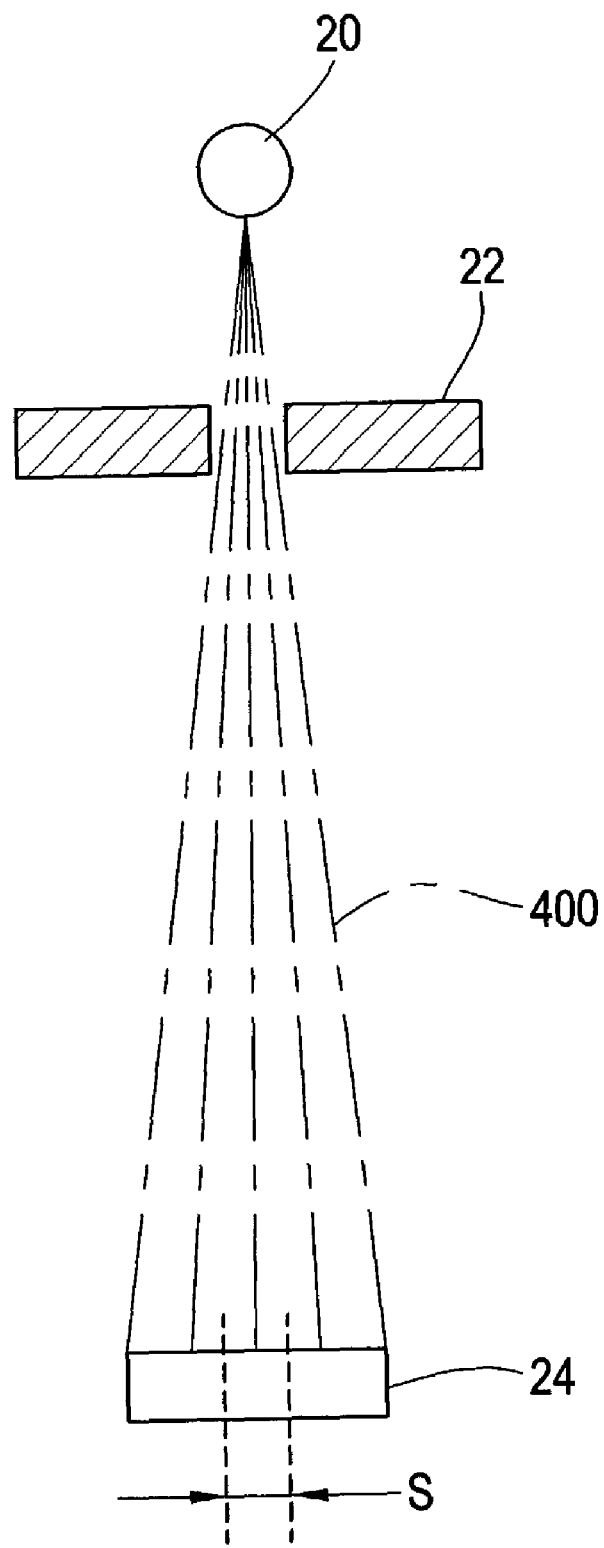
FIG. 6 picturesquely shows the X-ray irradiating/detecting device.

When the number of rows of detecting elements constituting the X-ray detector 24 is four, projection data representing projections of four sections is, as shown in FIG. 6, acquired at a time. The data processing unit 60 uses the projection data representing the projections of four sections to reconstruct an image.

Assuming that a distance between the centers of adjoining sections is s and a distance by which the X-ray irradiating/detecting device moves along the body axis during one rotation for helical scanning is L, L/s is regarded as a helical scan pitch.

Figure 7:
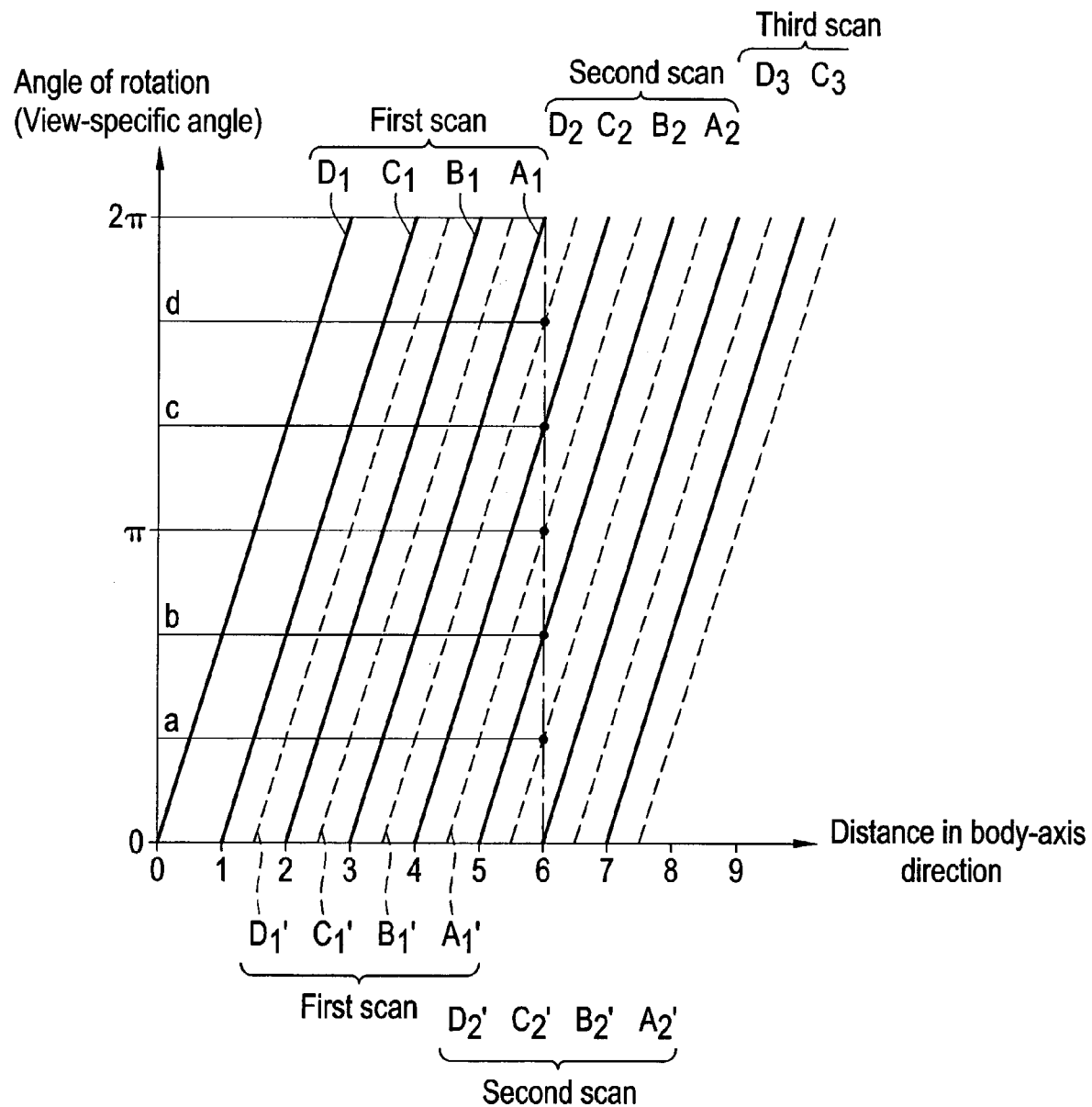
FIG. 7 graphically explains helical scanning.

When the helical scan pitch is set to, for example, 3, helical scanning is performed as shown in FIG. 7. Referring to FIG. 7, the axis of ordinates indicates an angle of rotation by which the X-ray irradiating/detecting device rotates, and the axis of abscissas indicates a distance in a body-axis direction by which the X-ray irradiating/detecting device moves. The distance in a body-axis direction is normalized by the distance s between the centers of adjoining sections.

Referring to FIG. 7, the initial position of the fourth row of detecting elements that is the last row in a direction of advancement shall be regarded as an origin of the system of coordinates. The initial position of the third row of detecting elements is separated from the origin by distance 1 in the direction of a body axis. The initial position of the second row of detecting elements is separated from the origin by distance 2 in the body-axis direction. The initial position of the first row of detecting elements is separated from the origin by distance 3 in the body-axis direction. The position of each row of detecting elements is represented by the position thereof attained when the row of detecting elements comes to the center of each section.

During helical scanning, the first row of detecting elements moves, as indicated with lines A in FIG. 7, from the position separated from the origin by distance 3 to the position separated therefrom by distance 6 with one rotation (one scan). Thereafter, the first row of detecting elements moves by distance 3 with each rotation. The second row of detecting elements moves, as indicated with lines B in FIG. 7, from the position separated from the origin by distance 2 to the position separated therefrom by distance 5 with the first scan, and thereafter moves by distance 3 with each rotation. The third row of detecting elements moves, as indicated with lines C in FIG. 7, from the position separated from the origin by distance 1 to the position separated therefrom by distance 4 with the first scan, and thereafter moves by distance 3 with each rotation. The fourth row of detecting elements moves, as indicated with lines D in FIG. 7, from the origin to the position separated from the origin by distance 3 with the first scan, and thereafter moves by distance 3 with each rotation. The number of rotations is indicated with a subscript of A, B, C, or D.

An angle of rotation is equivalent to an angle specific to each view. The lines A, B, C, and D indicate the positions on a body axis at each of which data stemming from a view, that is, view data is acquired. The lines A, B, C, and D indicate the positions from which the first, second, third, and fourth rows of detecting elements acquire data. As indicated with the lines A, B, C, and D, the position on the body axis at which view data is acquired is different from view to view.

Since the number of rows of detecting elements is four, four sets of view data are acquired with one scan. The positions at each of which data stemming from the same view is acquired are different from one another by distance 1 in the body-axis direction.

In the field of X-ray CT systems, a concept of opposite data is dealt with. What is referred to as opposite data is transmitted X-ray data acquired by irradiating X-rays at the same angle of irradiation in opposite directions. Assuming that transmitted X-ray data is acquired by rotating the X-ray irradiating/detecting device 360°, data acquired by rotating the X-ray irradiating/detecting device from 180° to 360° is opposite data relative to data acquired by rotating it from 0° to 180°.

Opposite data alone may be collected in order to form a data set. When an opposite data set is formed relative to each of the four sets of view data, four opposite data sets are available.

The opposite data set lags by an angle of rotation of 180°. This lag leads to a difference in a distance in the direction of a body axis that is equivalent to a half of the helical scan pitch. The positions at each of which opposite data relative to data acquired at a position indicated with each of lines A, B, C, and D is acquired are indicated with lines A', B', C', and D' that are dot lines. Incidentally, the subscripts appended to A', B', C', and D' each indicate the number of rotations.

As illustrated, line A1' is an intermediate between lines B2 and C2. Line B1' is an intermediate between lines C2 and D2. Since lines D2 and A1 are duplicate, line B1' may be said to be an intermediate between lines C2 and A1. Line C1' is an intermediate between lines A1 and B1, and line D1' is an intermediate between lines B1 and C1.

Hereinafter, a data set formed with data acquired at each of positions indicated with each of the lines A, B, C, and D may be called a real data set. A data set formed with data acquired at each of positions indicated with each of the lines A', B', C', and D' may be called an opposite data set.

All view data, that is, a plurality of data sets is used to reconstruct an image. For example, in order to reconstruct a tomographic image of a section separated from the origin by distance 6 as indicated with an alternate long and short dash line, data actually acquired from the slicing position while the X-ray irradiating/detecting device is rotated from 0 to $2\pi$, and interpolated data are needed.

The actually acquired data includes data acquired at an angle of rotation of 0 and contained in a real data set A2, data acquired at an angle of rotation of a and contained in an opposite data set C2', data acquired at an angle of rotation of b and contained in a real data set B2, data acquired at an angle of rotation of $\pi$ and contained in an opposite data set D2', data acquired at an angle of rotation of c and contained in a real data set C2, data acquired at an angle of rotation of d and contained in an opposite data set B1', and data acquired at an angle of rotation of $2\pi$ and contained in a real data set D2. The other data is produced through interpolation. For the interpolation, data contained in two data sets acquired at positions immediately preceding and succeeding the slicing position is used, that is, interpolated in order to produce intermediate data.

Prior to scanning, a dose is adjusted optimally to the object 8. The dose adjustment is achieved by adjusting the product of a tube current by a conduction time, that is, a milliampere-per-second (mAs) value. Hereinafter, the product of a tube current by a conduction time may be referred to simply as a tube current.

Figure 8:
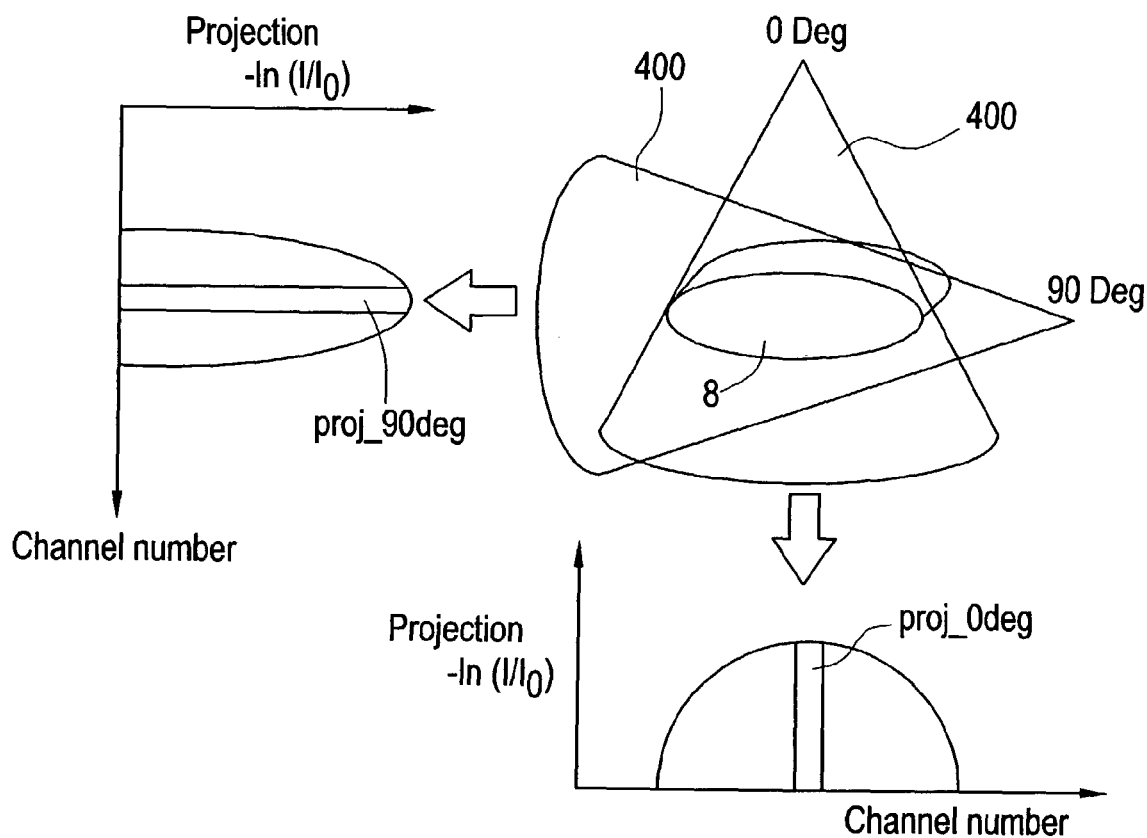
FIG. 8 is a conceptual diagram concerning scout radiography.

In order to adjust a tube current, a projection of the object 8 is measured. Specifically, as conceptually shown in FIG. 8, fluoroscopy is performed by irradiating the X-ray beam 400 to the object 8 at an angle of 0° (in the anteroposterior direction) and an angle of 90° (in a transverse direction). This results in projections. During fluoroscopy, the X-ray beam may be irradiated in a posteroanterior direction, that is, at an angle of 180° to the home position of the X-ray tube or X-ray irradiating/detecting device. Moreover, the X-ray beam is irradiated in the other transverse direction, that is, at an angle of 270° relative to the home position thereof. The fluoroscopy may be referred to as scout radiography.

The areas in the object whose projections are produced, that is, projection areas are calculated according to the formula below. The data processing unit 60 performs the calculation.

$$\text{projection\_area} = \sum_{i=1}^{i=\max\_ch} proj_{0deg\,i} \quad (1)$$

$$\text{projection\_area} = \sum_{i=1}^{i=\max\_ch} proj_{90deg\,i} \quad (2)$$

where i denotes a channel number, proj0deg i denotes projection data produced by irradiating the X-ray beam in the anteroposterior direction and acquired on each channel, and proj90deg i denotes projection data produced by irradiating the X-ray beam in one transverse direction and acquired on each channel. Whichever of the formulae (1) and (2) is used to calculate a projection area, the calculated value is the same.

The median of all projection data produced by irradiating the X-ray beam in the anteroposterior direction or transverse direction is calculated according to the following formula:

$$\text{proj\_0deg} = \sum_{i=cent-49}^{i=cent+50} proj_{0deg\,i} \quad (3)$$

-continued $$\text{proj\_90deg} = \sum_{i=cent-49}^{i=cent+50} proj_{90deg\,i} \quad (4)$$

where cent+50 denotes a value calculated by adding 50 to a center channel number, and cent−49 denotes a value calculated by subtracting 49 from the center channel number. Hereinafter, proj__0deg may be referred to as an anteroposterior median, and proj__90deg may be referred to as a transverse median.

Using the medians, the oval ratio of a section of the object 8 that shaped like an oval is calculated. The oval ratio is given as follows:

$$\text{oval\_ratio} = \frac{\sum_{i=cent-49}^{i=cent+50} proj_{90deg\,i}}{\sum_{i=cent-49}^{i=cent+50} proj_{0deg\,i}} \quad (5)$$

Incidentally, the above numerator and denominator are determined so that the oval ratio will be equal to or larger than 1. For example, when the head is examined, the anteroposterior median is larger than the transverse median. In this case, the anteroposterior median is assigned to the numerator, and the transverse median is assigned to the denominator. Whichever of the anteroposterior median and transverse median is larger, the larger one is concerned with the major axis of the oval, and the smaller one is concerned with the minor axis thereof.

The projection may be produced by irradiating X-rays in one of the anteroposterior and transverse directions during fluoroscopy. In this case, the projection area is calculated by adopting either the formula (1) or (2) according to the direction of fluoroscopy. The median of all projection data is calculated by adopting either the formula (3) or (4) according to the direction of fluoroscopy.

The relationship among a projection area, an anteroposterior median, and a transverse median is given as follows:

$$\text{projection\_area} = (\text{proj\_0deg} \times \text{proj\_90deg}) \times S \times I \quad (6)$$

where S denotes an oval coefficient, and I denotes an oval offset.

When two of the projection area, anteroposterior median, and transverse median are revealed, the other one can be worked out.

When fluoroscopy is performed by irradiating X-rays in either the anteroposterior or transverse direction, a projection area and a anteroposterior or transverse median are revealed. In this case, the other median is calculated as follows:

$$\text{proj\_orthogonal} = \frac{\text{projection\_area} - I}{\text{proj\_measure} \times S} \quad (7)$$

where proj__measure denotes a measured median.

Consequently, when proj_measure denotes a measured anteroposterior median, an oval ratio is calculated as follows:

$$\text{oval\_ratio} = \frac{\text{proj\_orthogonal}}{\text{proj\_measure}} \quad (8)$$

When proj_measure denotes a transverse median, the oval ratio is calculated as follows:

$$\text{oval\_ratio} = \frac{\text{proj\_measure}}{\text{proj\_orthogonal}} \quad (9)$$

Even in this case, the denominator and numerator must be determined so that the oval ratio will be equal to or larger than 1.

The quality of a reconstructed image is expressed in the form of an image SD. When a section of an object is circular, as long as a dose falls below a predetermined reference value, the image SD is a function of a projection area and given as follows:

$$\text{image\_SD} = \alpha + \beta \times \text{projection\_area} + \gamma \times \text{projection\_area}^2 \quad (10)$$

where α, β, and γ denote constants dependent on a tube voltage (kV) or the like.

When a section of an object is oval, the image SD varies depending on the oval ratio of the section. Assuming that a projection area remains constant, the relationship between the oval ratio and a change rate of the image SD is expressed as follows:

$$\text{SD\_ratio} = A + B \times \text{oval\_ratio}^2 \quad (11)$$

where A and B denote constants.

Figure 9:
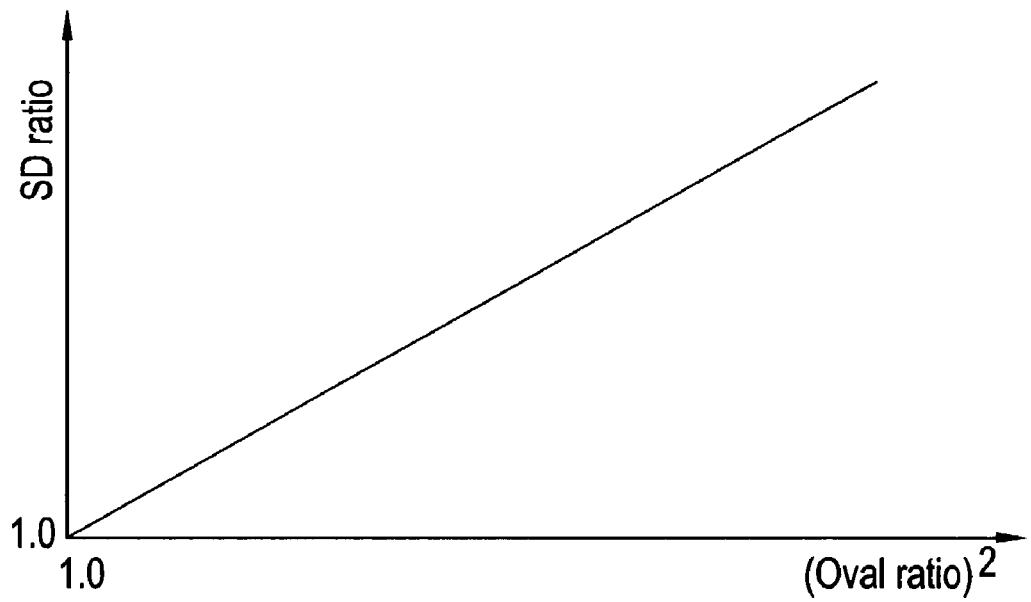
FIG. 9 is a graph indicating the relationship between an oval ratio and an SD ratio.

FIG. 9 is a graph indicating the relationship expressed as the formula (11). As seen from FIG. 9, when the oval ratio is 1, an SD ratio is 1. Namely, when a section of an object is circular, the image SD remains unchanged.

Owing to the above relationship, when a section of an object is oval, a modified image SD dependent on the sectional shape is calculated as follows:

$$\text{image\_SD}' = \text{image\_SD} \times \text{SD\_ratio} \quad (12)$$

The modified image SD is a predicted value of an image SD of a reconstructed image produced by imaging the object 8 using a reference dose of X-rays. Since a target value of the image SD is predetermined, the dose is determined so that the reconstructed image will be able to offer the image SD.

The relationship among the predicted value of the image SD, the reference dose, the target value of the image SD, and a required dose is given as follows:

$$\frac{\text{image\_SD}_{target}}{\text{image\_SD}_{predicted}} = \sqrt{\frac{mAs_{reference} \times \text{thickness\_factor}}{mAs_{scan}}} \quad (13)$$

where image_SDtarget denotes the target value of an image SD, image_SDpredicted denotes the predicted value thereof (=image_SD'), mAsreference denotes the reference dose, and mAsscan denotes the required dose.

$$\text{thickness\_factor} = \frac{10.0}{\text{thickness (mm)}} \quad (14)$$

wherein "thickness" denotes the thickness of the X-ray beam 400 at the isocenter for the object 8.

The required dose is derived from the formula (13) as follows:

$$mAs_{scan} = \frac{mAs_{reference} \times \text{thickness\_factor}}{\left[\frac{\text{image\_SD}_{target}}{\text{image\_SD}_{predicted}}\right]^2} \quad (15)$$

Consequently, a tube current is determined with the required dose as follows:

$$mAs_{scan} = \frac{mAs_{scan}}{\text{scan\_time(sec)}} \quad (16)$$

where scan_time denotes a scan time the X-ray CT system requires, that is, the time the X-ray irradiating/detecting device requires to make one rotation.

In the present X-ray CT system, the calculation of the tube current according to the above formula is performed for each of four angular ranges defined by quartering an angle of rotation to be cleared with one rotation of the X-ray irradiating/detecting device. The four angular ranges are, for example, angular ranges defined with an angle of 90° as shown in FIG. 9. The angular ranges shall be called orderly clockwise as sectors 1, 2, 3, and 4. Sectors 1 and 3 cover ±45° with respect to the anteroposterior or posteroanterior direction. Sectors 2 and 4 cover ±45° with respect to a transverse direction.

Figure 10:
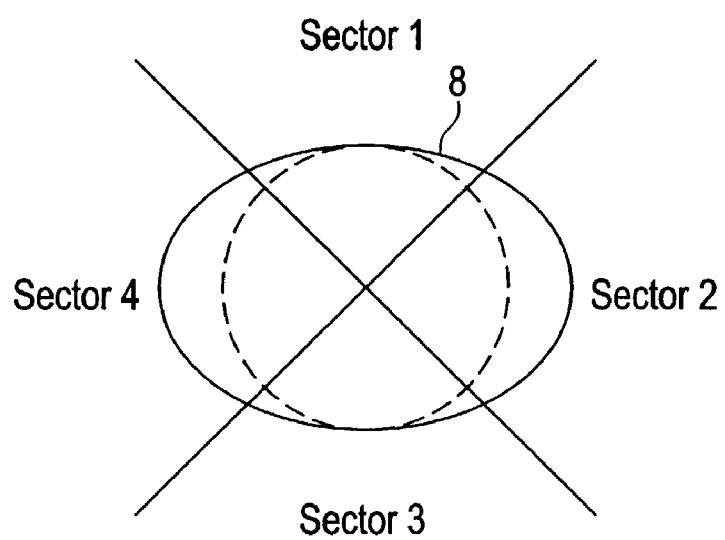
FIG. 10 shows the relationship between a section of an object of imaging and sectors.

FIG. 10 shows a section of the object 8 that is shaped like an oval compressed in the anteroposterior direction. The trunk of the object 8 generally has such a sectional shape. Assuming that a circle is inscribed on the oval of the section as indicated with a dot line, a difference between the oval and circle is small in sectors 1and 3. In sectors 1 and 3, therefore, the section of the object 8 may be regarded as a substantially circular plane. The oval ratio calculated according to the formula (5), (8), or (9) is therefore not adopted but the oval ratio of a circle, that is, 1 is adopted. In contrast, in sectors 2 and 4, the oval ratio calculated according to the formula (5), (8), or (9), that is, the real oval ratio is adopted.

As mentioned above, the oval ratio is set to different values between sectors 1 and 3 and sectors 2 and 4. The SD ratio given by the formula (11) is therefore different between sectors 1 and 3 and sectors 2 and 4. Accordingly, the predicted value of the image SD, that is, image_SD' in the formula (12) differs between sectors 1and 3 and sectors 2 and 4. Consequently, when the predicted value of the image SD is assigned to the formula (15), a dose becomes different between sectors 1and 3 and sectors 2 and 4. Although the dose is different, since the target value of the image SD employed in calculating the dose is the same, the quality of a reconstructed image will remain unaffected.

The dose for sectors 2 and 4 is calculated using the real oval ratio of the section of the object 8, and is appropriate for radiography having X-rays irradiated in a transverse direction to the oval section compressed in the anteroposterior direction. Needles to say, the dose is transformed into a tube current according to the formula (16). The same applies to the description below.

The dose for sectors 1 and 3 is calculated with the oval ratio of the section of the object 8 regarded as 1, and is therefore smaller than the dose for sectors 2 and 4. This reduction in the dose is proportional to a difference by which an X-ray transmissivity on sectors 1 and 3 is smaller than an X-ray transmissivity on sectors 2 and 4. The reduction in the dose is therefore appropriate. The dose is thus reduced for sectors 1 and 3 that correspond to a half of an angular range in an object that is exposed during one rotation of the X-ray irradiating/detecting device. This leads to a reduction in a patient exposure by which the object 8 is exposed to X-rays during one scan.

Figure 11:
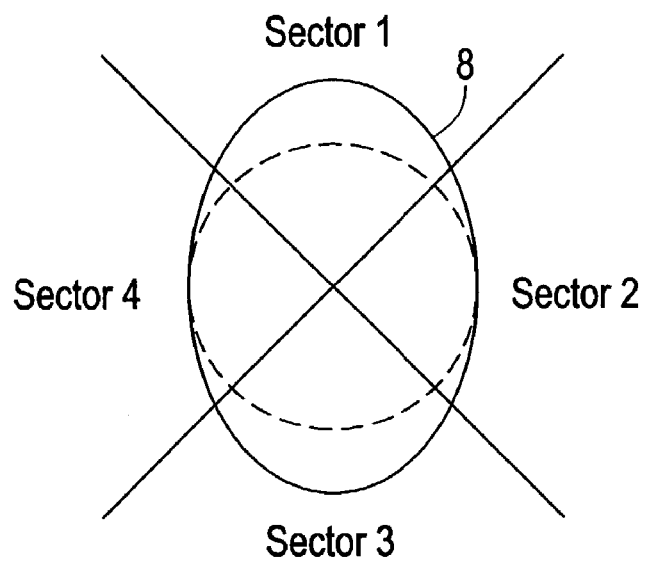
FIG. 11 shows the relationship between a section of an object of imaging and sectors.

The sectional shape of the head of the object 8 is, as shown in FIG. 11, an oval compressed in transverse directions. In this case, the oval ratio of the section is adapted to sectors 1 and 3, and the oval ratio of 1 is adapted to sectors 2 and 4. The dose is calculated for the sectors using the oval ratios, whereby the dose optimal to each pair of sectors can be calculated. Moreover, the patient exposure by which the object 8 is exposed to X-rays during one scan can be reduced.

As mentioned above, the dose is optimized by distinguishing directions in which a section of an object is compressed from directions perpendicular to the directions. Consequently, an excess or shortage of a dose can be avoided and the patient exposure of the object 8 can be reduced.

Whether a oval section is compressed in the anteroposterior and posteroanterior directions or the transverse directions is judged from, for example, a ratio of an anteroposterior median to a transverse median, that is, a quotient of the anteroposterior median by the transverse median. When the ratio is smaller than 1, the oval section is compressed in the anteroposterior and posteroanterior directions. When the ratio is equal to or larger than 1, the oval section is compressed in the transverse directions. The ratio used as a criterion may be replaced with an inverse number of the ratio. In this case, when the ratio is equal to or larger than 1, the oval section is compressed in the anteroposterior and posteroanterior directions When the ratio is smaller than 1, the oval section is compressed in the transverse directions.

When an oval section of an object is compressed in the anteroposterior and posteroanterior directions, the angular ranges to which the oval ratio of 1 is adapted are sectors 1 and 3. When the oval section thereof is compressed in the transverse directions, the angular ranges are sectors 2 and 4. Preferably, the angular ranges are adjusted based on the compression of an oval section. Hereinafter, the angular ranges to which the oval ratio of 1 is adapted may be referred to as dose reduction ranges.

Figure 12:
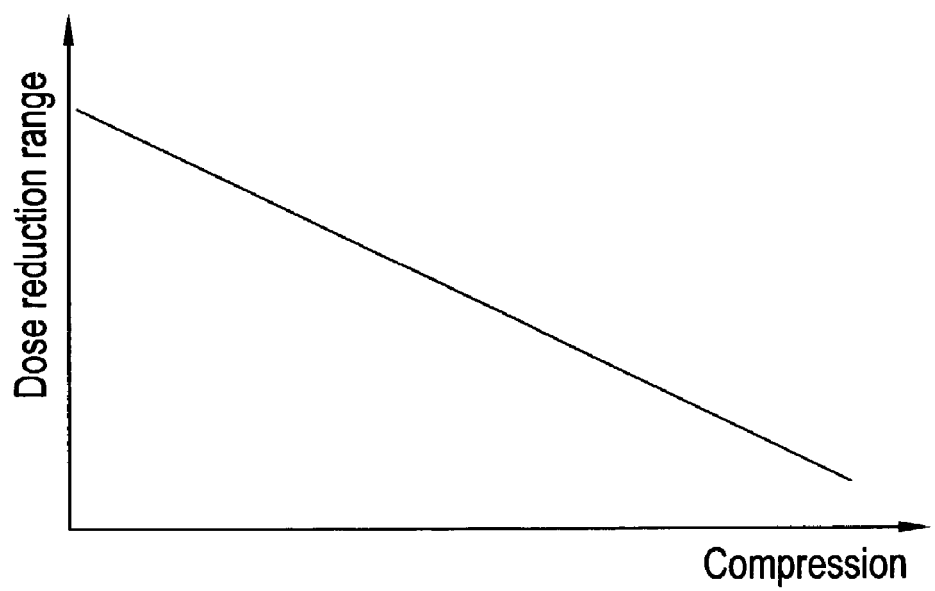
FIG. 12 shows the relationship between the compression of an oval section and dose reduction ranges.
Figure 13A:
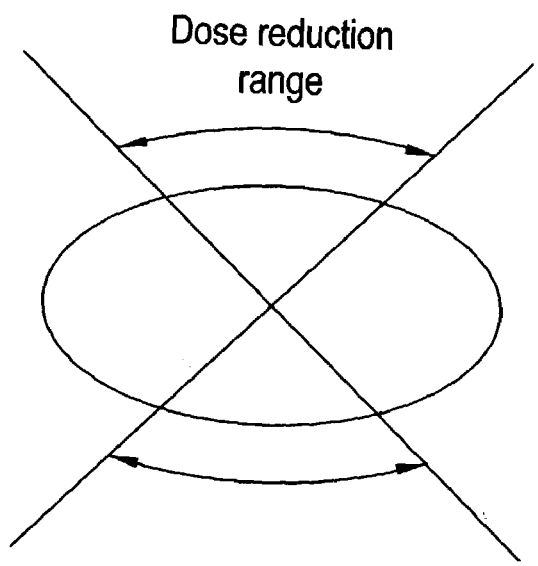
FIG. 13 shows widened dose reduction ranges and narrowed dose reduction ranges.
Figure 13B:
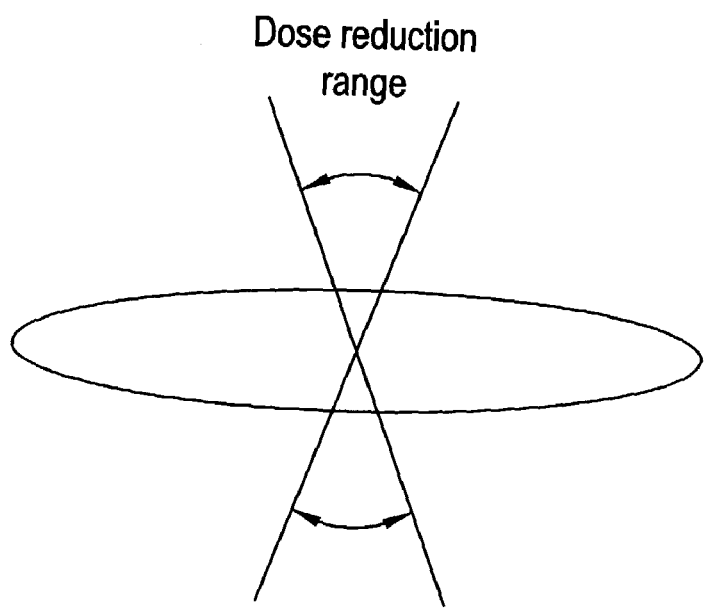

The dose reduction ranges are, as graphically shown in FIG. 12, narrowed in proportion to an increase in the compression. Incidentally, the compression is expressed as a ratio of the major-axis length of an oval to the minor-axis length thereof. Consequently, when the compression of a section is small, the dose reduction ranges that fan out at 90° with the minor axis as a centerline are defined as shown in FIG. 13a. When the compression of a section is large, the dose reduction ranges that fan out at 45° with the minor axis as a centerline are defined as shown in FIG. 13b. The angular ranges other than the dose reduction ranges are dose non-reduction ranges. A change in the dose non-reduction ranges is the reverse of the change in the dose reduction ranges.

As mentioned above, the dose reduction ranges are widened or narrowed depending on the compression of a section. Consequently, a range to which X-rays of a small dose are irradiated is optimized. Eventually, the incident that the dose is locally short can be avoided. The data processing unit 60 judges whether the dose reduction ranges should be widened or narrowed. The data processing unit 60 is an example of an embodiment of an angular range adjusting means included in the present invention.

Figure 14:
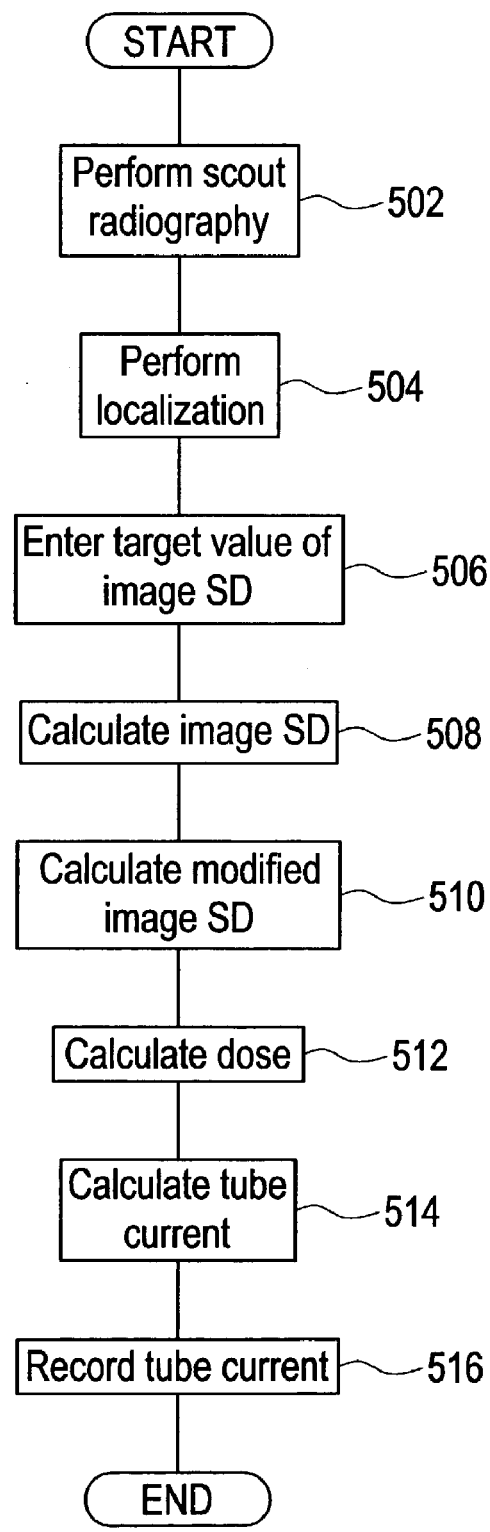
FIG. 14 is a flowchart describing the actions of a system of an example of an embodiment of the present invention.

FIG. 14 is a flowchart describing a procedure from a step of scout radiography to a step of dose calculation. As described in FIG. 14, at step 502, scout radiography is carried out. During the scout radiography, X-rays are irradiated to the object over a predetermined range along the body axis of the object in either the anteroposterior or transverse direction. This results in projections of sections extending at positions on the body axis.

At step 504, localization is carried out. The localization is such that a scan start point and a scan end point are determined in a body-axis direction in a fluoroscopic image resulting from the scout radiography. Consequently, for example, when helical scanning is performed, slicing positions are determined based on the helical scan pitch. A user handles the operating unit 70 so as to achieve the localization.

At step 506, a target value of an image SD is entered. The user handles the operating unit 70 so as to enter the target value. When a standard value preserved in advance in the X-ray CT system is adopted as the target value of the image SD, entry is omitted (a default value is adopted).

At step 508, the image SD is calculated. In the calculation of the image SD, a projection area is determined first. When scout radiography is performed by irradiating X-rays in the anteroposterior and transverse directions, the projection area is calculated according to the formulas (1) and (2). When scout radiography is performed by irradiating X-rays in either of the anteroposterior direction and transverse direction, the projection area is calculated according to the formula (1) or (2) dependent on the direction. The calculated projection area is assigned to the formula (10) in order to calculate the image SD. The image SD is calculated for each group of slicing positions determined with the helical scan pitch. The same applies to calculations described below.

At step 510, a modified image SD is calculated. Prior to the calculation of the modified image SD, an anteroposterior median and a transverse median are calculated according to the formulas (3) and (4), and an oval ratio is calculated according to the formula (5). Otherwise, the anteroposterior median or transverse median is calculated according to the formula (3) or (4), the transverse median or anteroposterior median is calculated according to the formula (7), and the oval ratio is calculated according to the formula (8) or (9).

The oval ratio is assigned to the formula (11) in order to calculate an SD ratio. The SD ratio is assigned to the formula (12) in order to calculate the modified image SD. The modified image SD is calculated for sectors 1 and 3 separately from it is for sectors 2 and 4. In this case, since the oval ratio is set to 1 for the sectors that are the compressed portions of a section, the modified image SD is the same as the non-modified one. Therefore, the calculation of the modified image SD for the sectors that are the compressed portions of a section may be omitted, and the non-modified image SD may be adopted as the modified one.

At step 512, a dose is calculated according to the formula (15). The target value of the image SD entered at step 506 is assigned as image_SDtarget to the formula (15). The two modified image SD values are assigned as image_SDpredicted. This results in two dose values.

Figure 15:
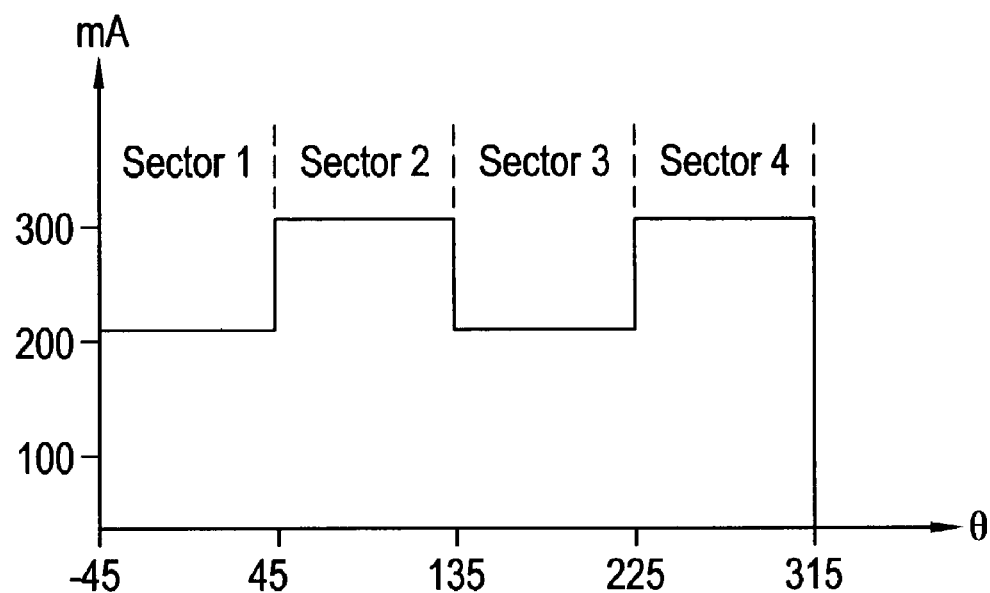
FIG. 15 shows the relationship between sectors and a tube current.

At step 514, a tube current is calculated according to the formula (16). Since the dose assumes two values, two tube current values are calculated. FIG. 15 graphically shows an example of the thus calculated tube current. As graphically shown in FIG. 15, for example, 200 mA is calculated for sectors 1 and 3, and 300 mA is calculated for sectors 2 and 4.

Figure 16:
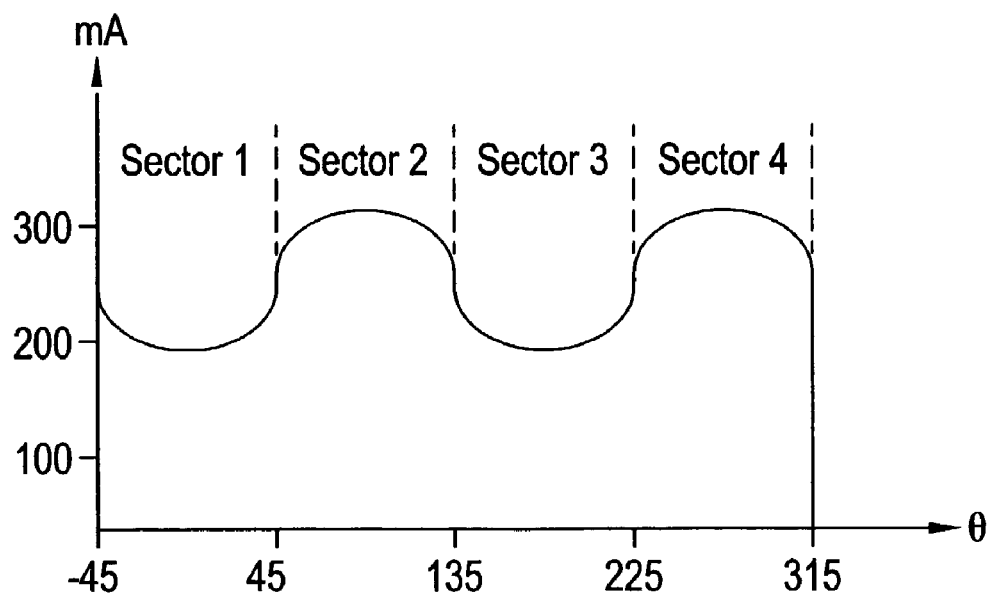
FIG. 16 shows the relationship between sectors and a tube current.

Instead of switching the current values stepwise, the current values may be, as shown in FIG. 16, varied so that they will be plotted as sine waves. In this case, a continuous change in an X-ray transmissivity on an oval section which depends on an angle of rotation $\theta$ can be coped with.

FIG. 15 and FIG. 16 are concerned with a case where a section is oval and compressed in the anteroposterior and posteroanterior directions. When a section is oval and compressed in the transverse directions, the current value for sectors 1 and 3 and the current value for sectors 2 and 4 are switched.

At step 516, the tube current values for the pairs of sectors are stored in a memory. Consequently, the tube current values are preserved in association with the pairs of sectors and the group of slicing positions determined with the helical scan pitch.

Figure 17:
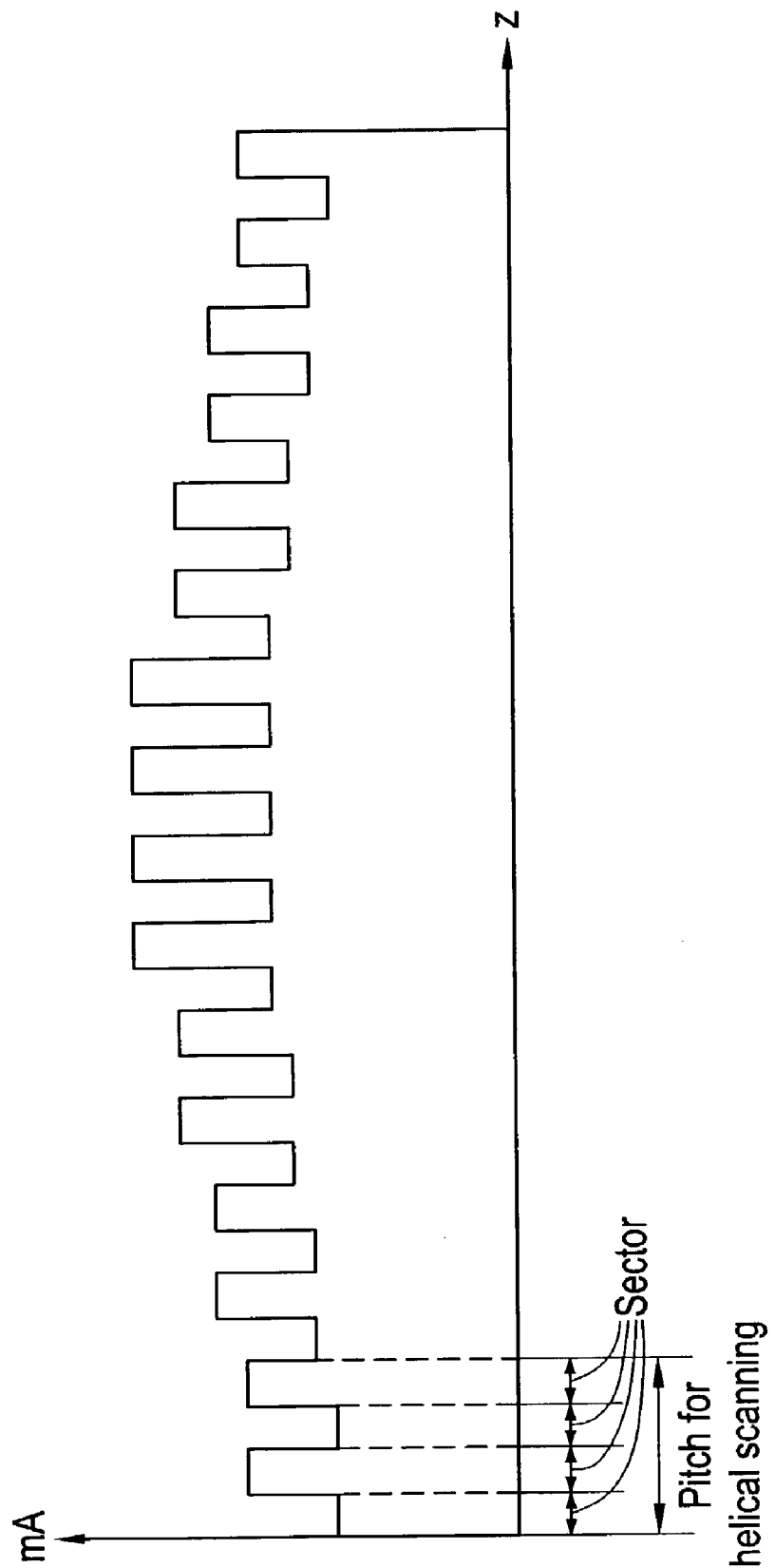
FIG. 17 shows the relationship between the positions on a body axis to which X-rays are irradiated and a tube current.

During helical scanning, the position of one sector on a body axis differs from the position of any other sector. Therefore, the tube current values are recorded in association with positions on the body axis. FIG. 17 shows an example of the tube current values recorded in association with the positions on the body axis. Referring to FIG. 17, a variation of an envelope plotted by linking the points indicating the tube current values corresponds to a variation of a projection of the object 8 dependent on the position on the body axis. Needless to say, the tube current may vary depending on the position on the body axis so that the variation will be graphically expressed as sine waves. The thus recorded tube current values are successively read with the progress of scanning. The read value is used as a reference value to adjust an actual tube current.

When a direction of X-irradiation to be made at the start of scanning remains constant, for example, is a direction at 0°, the recorded tube current values are read orderly from the one for sector 1. However, when the direction in which X-rays are irradiated at the start of scanning is not constant, if the recorded tube current values are read orderly from the one for sector 1, an actual tube current may not be able to be adjusted properly.

Figure 18:
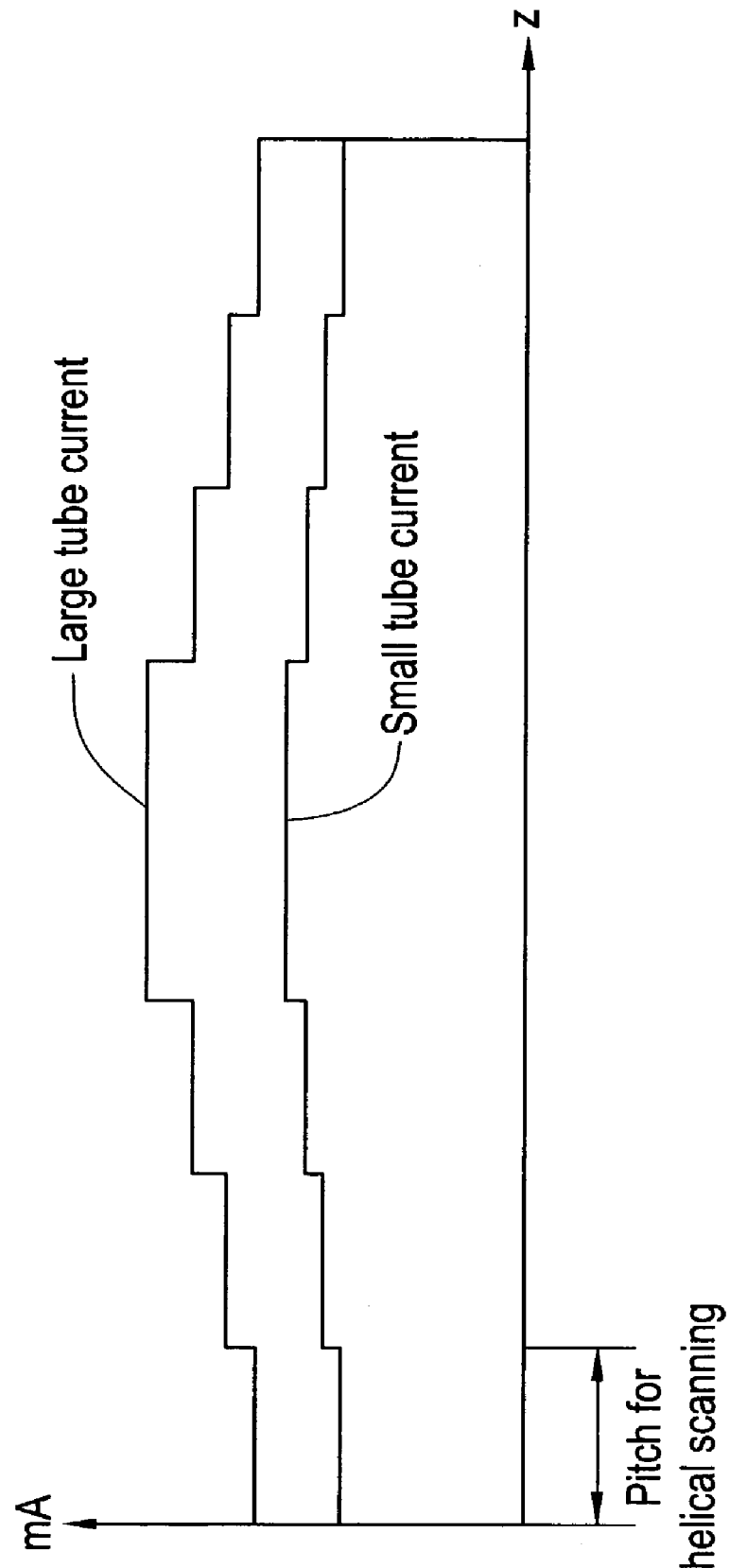
FIG. 18 shows the relationship between the positions on a body axis to which X-rays are irradiated and tube current values.

When the direction of X-irradiation to be made at the start of scanning is not constant, the two kinds of tube current values, that is, large and small tube current values are, as shown in FIG. 18, calculated for each position on a body axis irrespective of a sector. The calculated current values are recorded in association with each group of slicing positions determined with the helical scan pitch. The positions on the body axis are involved in specific views. Therefore, the two kinds of tube current values maybe said to be recorded in association with the views. The data processing unit 60 calculates the tube current values. The data processing unit 60 is an example of an embodiment of a dose calculating means included in the present invention.

The first X-irradiation to be performed at the start of scanning depends on the small tube current values out of the recorded tube current values. Immediately after the start of scanning, an angle-of-rotation signal representing an angle of rotation made by the X-ray irradiating/detecting device is fed back. A sector to be exposed to X-rays irradiated at the angle of X-irradiation is identified. If the sector is one of sectors 1 and 3, the small tube current values are selected from the two kinds of tube current values. If the sector is one of sectors 2 and 4, the large tube currents are selected from the two kinds of tube current values. X-rays are then irradiated using the selected tube current values as references. Thereafter, every time sectors are switched, associated tube current values are selected. Consequently, even when the direction of X-irradiation is not constant at the start of scanning, an actual tube current can be adjusted properly. The data processing unit 60 selects either of the two kinds of tube current values. The data processing unit 60 is an example of an embodiment of a dose adapting means included in the present invention.

When the helical scan pitch is large, a change in a projection area occurring during one scan is large. Even when the helical scan pitch is not so large, the change in a projection area occurring during one scan may be large though it depends on a radiographic region. In this case, the calculated tube current values may not always be appropriate.

Assume that helical scanning is performed with the helical scan pitch set to a large value, or that a region whose projection area changes largely during one scan is scanned. In this case, tube current calculation is not performed for each group of slicing positions determined with the helical scan pitch but performed for each rotational extent smaller than the rotation covering the group of slicing positions determined with the helical scan pitch. The rotational extent is, for example, a quarter of the helical scan pitch but not limited to this value. Alternatively, the rotational extent may be larger than one quarter as long as it is smaller than the rotation covering the group of slicing positions determined with the helical scan pitch or may be smaller than one quarter. The rotational extent matches an angular range defined with each sector. By the way, the positions of the sectors on a body axis are different from one another.

In order to calculate a tube current value for each sector, calculation of an image SD described as step 508 in the flowchart of FIG. 14 is performed for each sector but not for each group of slicing pitches determined with the helical scan pitch. Specifically, a projection area within each sector is calculated, and the image SD is calculated based on the projection area. When the projection area is different from sector to sector, a calculated image SD value varies depending on a sector.

At step 510, only one modified image SD value is calculated. Talking of an oval ratio needed to calculate the modified image SD value, the oval ratio of a section containing a sector concerned is adopted or 1 is adopted. If a sector contains the major axis of an oval section, the oval ratio of the section is adopted. If the sector contains the minor axis thereof, 1 is adopted.

Figure 19:
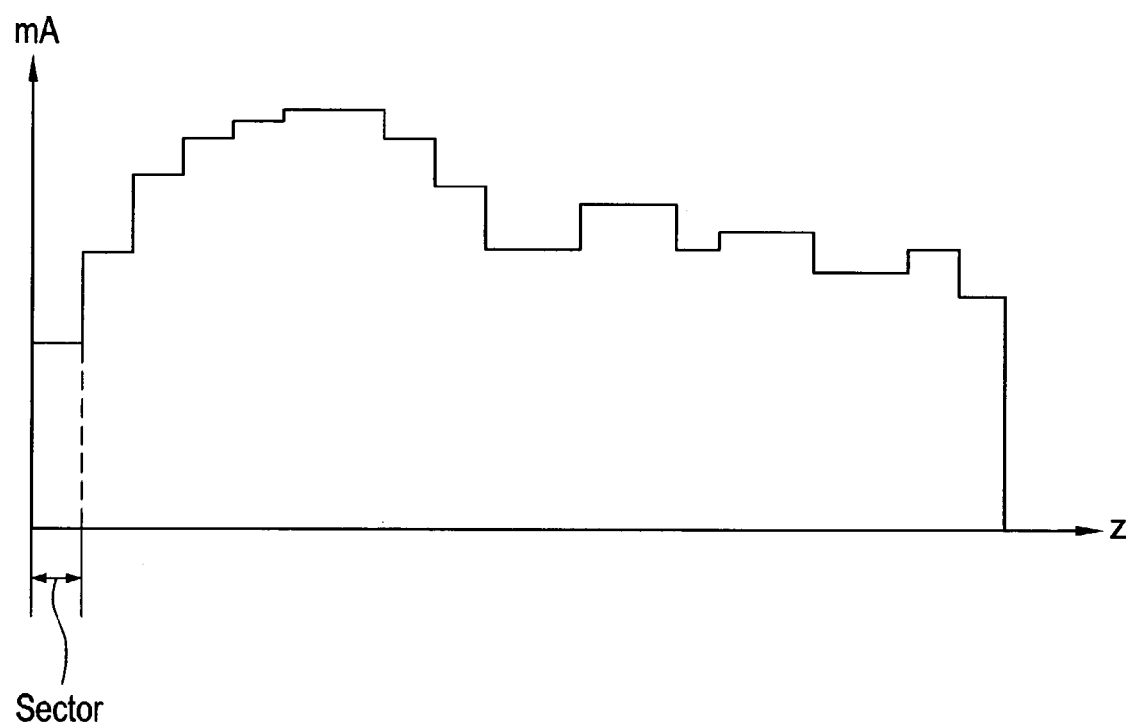
FIG. 19 shows the relationship between the positions on a body axis to which X-rays are irradiated and a tube current.

At steps 512 and 514, the modified image SD is used to calculate a dose value and a tube current value. Consequently, tube current values for sectors are calculated, and stored in a memory at step 516. In this case, the stored or recorded tube current values are expressed, for example, as graphically as shown in FIG. 19.

Figure 20:
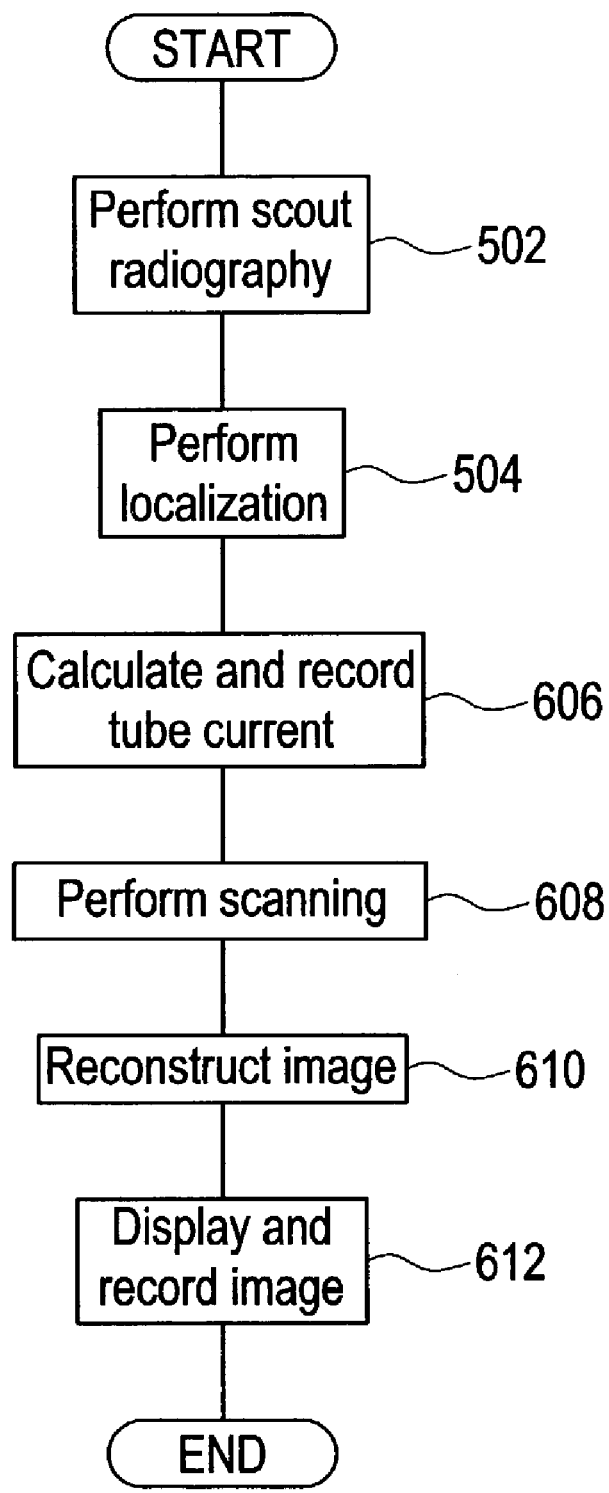
FIG. 20 is a flowchart describing the actions of the system of an example of an embodiment of the present invention.

All actions to be performed by the present X-ray CT system will be outlined below. FIG. 20 is a flowchart describing all the actions to be performed by the present X-ray CT system. As described in FIG. 20, the aforesaid scout radiography and localization are performed at steps 502 and 504 respectively.

At step 606, tube current values are calculated and recorded. The details of step 606 are described as steps 506 to 516 in FIG. 14 This results in tube current data shown in FIG. 18 or FIG. 19.

At step 608, scanning is performed. In the course of scanning, the recorded tube current values are successively read in association with the positions on a body axis to which X-rays are irradiated. An actual tube current is adjusted using the read value as a reference. Consequently, X-rays of a dose optimal to each sector are irradiated.

The data processing unit 60 controls the X-ray controller 28 via the control interface 62, whereby tube current adjustment is achieved. The data processing unit 60, control interface 62, and X-ray controller 28 constitute an example of an embodiment of a dose adjusting means included in the present invention.

At step 610, an image is reconstructed. Since X-rays of a dose optimal to each sector are irradiated, the patient exposure of the object 8 can be minimized and a high-quality image can be reconstructed. The image data is stored in a memory with the image displayed on the display device 69 at step 612.

A case where helical scanning is performed has been described so far. The present invention is not limited to helical scanning. Even when the present invention is adapted to axial transverse scanning, the same advantages as those described above can be provided according to the aforesaid method.

The present invention has been described by taking a preferred embodiment for instance. A person having an ordinary knowledge of the technical field to which the present invention belongs can make various modifications or replacements of the aforesaid embodiment without a departure from the technical scope of the present invention. Consequently, the technical scope of the present invention encompasses not only the aforesaid embodiment but also all forms described in Claims.

The invention claimed is:

1. A system comprising:
an X-ray tube;
data acquiring means for rotating an X-ray irradiating/detecting device, which includes an X-ray irradiator that has said X-ray tube and irradiates a fan-shaped X-ray beam and an X-ray detector that has a plurality of X-ray detecting elements arrayed in a direction in which the fan-shaped X-ray beam spreads and that is opposed to said X-ray irradiator with an object of imaging between them, about the object so as to acquire transmitted X-ray data stemming from a plurality of views;
dose adjusting means for differentiating dose values of the X-ray beam between predetermined angular ranges of a section of the object shaped like an oval, which extend with the minor axis of the section as a center-line, and the other angular ranges thereof; and
dose calculating means for calculating the dose values based on a specific target value of a standard deviation of an image, the standard deviation input independent of a reference value of a tube current designated to flow through said X-ray tube.

2. The system according to claim 1, wherein the predetermined angular ranges are adjusted based on compression of the section of the object shaped like an oval.

3. The system according to claim 1, wherein said dose calculating means calculates in advance the dose values of the X-ray beam for each position on the body axis of the object through which the X-ray beam passes, and said dose calculating means calculates the dose values based on one of a first assumption that the section of the object is shaped like an oval and a second assumption that the section of the object is shaped like a circle, and said system further comprising dose adopting means for selecting either of the dose values according to the angular ranges to either of which said X-ray irradiating/detecting device is moved by an angle of rotation.

4. The system according to claim 1, wherein said dose calculating means calculates the dose values based on an image SD predicted from a projection of the object created by X-rays.

5. The system according to claim 1, wherein the specific target value of the standard deviation of the image is manually adjustable.

6. The system according to claim 1, wherein said dose adjusting means adjusts the dose values based on a tube current flowing through said X-ray tube.

7. The system according to claim 1, wherein said data acquiring means rotates said X-ray irradiating/detecting device about the object along a helical trajectory.

8. An X-ray computed tomography system comprising:
an X-ray tube;
data acquiring means for rotating an X-ray irradiating/detecting device, which includes an X-ray irradiator that has said X-ray tube and irradiates a fan-shaped X-ray beam and an X-ray detector that has a plurality of X-ray detecting elements arrayed in a direction in which the fan-shaped X-ray beam spreads and that is opposed to said X-ray irradiator with an object of imaging between them, about the object so as to acquire transmitted X-ray data stemming from a plurality of views;
dose adjusting means for differentiating dose values of the X-ray beam between predetermined angular ranges of a section of the object shaped like an oval, which extend with the minor axis of the section as a center-line, and the other angular ranges thereof;
dose calculating means for calculating the dose values based on a specific target value of a standard deviation of an image, the standard deviation input independent of a reference value of a tube current designated to flow through said X-ray tube; and
image producing means for producing an image on the basis of the transmitted X-ray data.

9. The X-ray computed tomography system according to claim 8, wherein the predetermined angular ranges are adjusted based on compression of the section of the object shaped like an oval.

10. The X-ray computed tomography system according to claim 8, wherein said dose calculating means calculates in advance the dose values of the X-ray beam for each position on the body axis of the object through which the X-ray beam passes, and said dose calculating means calculates the dose values based on one of a first assumption that the section of the object is shaped like an oval and a second assumption that the section of the object is shaped like a circle, and said transmitted X-ray data acquisition system further comprising dose adopting means for selecting either of the dose values according to the angular ranges to either of which said X-ray irradiating/detecting device is moved by an angle of rotation.

11. An X-ray computed tomography system according to claim 10, wherein said dose calculating means calculates the dose values based on an image SD predicted from a projection of the object created with X-rays.

12. The X-ray computed tomography system according to claim 11, wherein the specific target value of the standard deviation of the image is manually adjustable.

13. An X-ray computed tomography system according to claim 8, wherein said dose adjusting means adjusts the dose values based on a tube current flowing through said X-ray tube.

14. The X-ray computed tomography system according to claim 8, wherein said data acquiring means rotates said X-ray irradiating/detecting device about the object along a helical trajectory.

* * * * *

UNITED STATES PATENT AND TRADEMARK OFFICE
CERTIFICATE OF CORRECTION

PATENT NO. : 6,987,828 B2 Page 1 of 1
APPLICATION NO. : 10/397026
DATED : January 17, 2006
INVENTOR(S) : Horiuchi It is certified that error appears in the above-identified patent and that said Letters Patent is hereby corrected as shown below:

In Claim 2, column 19, line 65, delete "based on compression" and insert therefor -- based on a compression --.

In Claim 9, column 20, line 56, delete "based on compression" and insert therefor -- based on a compression --.

Signed and Sealed this

Third Day of June, 2008

JON W. DUDAS
*Director of the United States Patent and Trademark Office*